United States Patent
Wang et al.

(10) Patent No.: US 8,779,779 B2
(45) Date of Patent: Jul. 15, 2014

(54) ON-CHIP CELL MIGRATION DETECTION

(75) Inventors: Lei Wang, Beijing (CN); Jing Zhu, Beijing (CN); Cheng Deng, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 644 days.

(21) Appl. No.: 12/288,971

(22) Filed: Oct. 24, 2008

(65) Prior Publication Data

US 2009/0251155 A1 Oct. 8, 2009

(30) Foreign Application Priority Data

Apr. 8, 2008 (CN) .......................... 2008 1 0103526

(51) Int. Cl.
*G01R 27/28* (2006.01)

(52) U.S. Cl.
USPC ..................... 324/649; 435/287.1; 435/288.5; 435/297.5; 435/286.1; 435/401; 204/600

(58) Field of Classification Search
USPC ................ 324/688, 649; 435/287.1, 32, 401, 435/288.5, 297.5, 173.1, 173.4, 286.1
See application file for complete search history.

(56) References Cited

U.S. PATENT DOCUMENTS

| | | | |
|---|---|---|---|
| 3,513,384 A | 5/1970 | Schneider | |
| 4,920,047 A | 4/1990 | Giaever et al. | |
| 5,187,096 A | 2/1993 | Giaever et al. | |
| 6,437,551 B1 | 8/2002 | Krulevitch et al. | |
| 6,758,961 B1 | 7/2004 | Vogel et al. | |
| 7,462,324 B2 | 12/2008 | Ozaki et al. | |
| 7,833,396 B2 | 11/2010 | Fukushima | |
| 2002/0182591 A1* | 12/2002 | Giaever et al. | ................ 435/4 |
| 2004/0128633 A1 | 7/2004 | Weller et al. | |
| 2004/0152067 A1 | 8/2004 | Wang et al. | |
| 2004/0163953 A1* | 8/2004 | Bhullar et al. | ........... 204/403.01 |
| 2005/0004442 A1 | 1/2005 | Ozaki et al. | |
| 2005/0067279 A1 | 3/2005 | Chen et al. | |
| 2005/0130119 A1 | 6/2005 | Giaever et al. | |

(Continued)

FOREIGN PATENT DOCUMENTS

| | | |
|---|---|---|
| CN | 1996001 A | 7/2007 |
| TW | 2008/30963 A | 7/2008 |
| WO | 2004/010102 A2 | 1/2004 |
| WO | 2004/010103 A2 | 1/2004 |

OTHER PUBLICATIONS

Arndt, S., et al., "Bioelectrical Impedance Assay to Monitor Changes in Cell Shape During Apoptosis," Biosensors and Bioelectronics, 19(6):583-594, Jan. 2004.

(Continued)

*Primary Examiner* — Arleen M Vazquez
*Assistant Examiner* — Son Le
(74) *Attorney, Agent, or Firm* — Perkins Coie LLP

(57) ABSTRACT

Techniques, systems and apparatus are disclosed for detecting impedance. In one aspect, a microelectrode sensing device includes a substrate and an array of microelectrode sensors formed on the substrate. Each sensor includes at least one conductive layer formed above the substrate and patterned to include a counter electrode and multiple sensing electrodes to detect an electrical signal in absence and presence of one or more target cells positioned on at least a portion of a surface of each sensing electrode. The sensing electrodes are spaced apart and arranged around the counter electrode to provide a spatially averaged value of the detected electrical signal.

29 Claims, 14 Drawing Sheets

(56) References Cited

U.S. PATENT DOCUMENTS

| | | | |
|---|---|---|---|
| 2005/0153425 A1 | 7/2005 | Xu et al. | |
| 2005/0213374 A1 | 9/2005 | Xu et al. | |
| 2005/0252777 A1* | 11/2005 | Li | 204/600 |
| 2006/0105321 A1 | 5/2006 | Moy et al. | |
| 2006/0121446 A1 | 6/2006 | Abassi et al. | |
| 2006/0151324 A1* | 7/2006 | Davies et al. | 204/484 |
| 2006/0188904 A1 | 8/2006 | Ozkan et al. | |
| 2007/0155015 A1 | 7/2007 | Vassanelli et al. | |
| 2007/0228403 A1 | 10/2007 | Choi et al. | |
| 2007/0296425 A1 | 12/2007 | LaMeres et al. | |
| 2008/0083617 A1* | 4/2008 | Simpson et al. | 204/403.1 |
| 2008/0106884 A1 | 5/2008 | English et al. | |
| 2008/0286750 A1 | 11/2008 | Xu et al. | |
| 2009/0057147 A1 | 3/2009 | Kayyem | |
| 2009/0322309 A1 | 12/2009 | Zhu et al. | |
| 2010/0184115 A1 | 7/2010 | Lei et al. | |
| 2010/0264024 A1* | 10/2010 | Fukushima | 204/403.01 |

OTHER PUBLICATIONS

Bieberich, E., et al., "Neuronal Differentiation and Synapse Formation of PC12 and Embryonic Stem Cells on Interdigitated Microelectrode Arrays: Contact Structures for Neuron-to-Electrode Signal Transmission (NEST)," Biosensors and Bioelectronics, 19(8):923-931, Mar. 2004.

Giaever, I., et al., "Micromotion of Mammalian Cells Measured Electrically," Proceedings of the National Academy of Science of the USA, 88(17):7896-7900, Sep. 1991.

Giaever, I., et al., "Monitoring Fibroblast Behavior in Tissue Culture with an Applied Electric Field," Proceedings of the National Academy of Science of the USA, 81(12):3761-3764, Jun. 1984.

Huang, X., et al., "Simulation of microelectrode impedance changes due to cell growth," IEEE Sensors Journal, 4(5):576-583, 2004.

Wegener, J., et al., "Electric Cell-Substrate Impedance Sensing (ECIS) as a Noninvasive Means to Monitor the Kinetics of Cell Spreading to Artificial Surfaces," Experimental Cell Research, 259(1):158-166, Aug. 2000.

Xiao, C., et al., "An in-depth analysis of electric cell-substrate impedance sensing to study the attachment and spreading of mammalian cells," Analytical Chemistry, 74(6):1333-1339, Feb. 2002.

Xiao, C., et al., "Online Monitoring of cell growth and cytotoxicity using electric cell-substrate impedance sensing (ECIS)," Biotechnology Progress, 19:1000-1005, 2003.

Xing, J.Z., et al., "Dynamic Monitoring of Cytotoxicity on Microelectronic Sensors," Chemical Research in Toxicology, 18(2):154-161, Feb. 2005.

Yu, N., et al., "Real-time monitoring of morphological changes in living cells by electronic cell sensor arrays : An approach to study G protein-coupled receptors," Analytical Chemistry, 78(1):35-43, Jan. 2006.

International Search Report dated Feb. 28, 2008 for International Application No. PCT/CN2007/002260, filed Jul. 25, 2007 (4 pages).

European Search Report dated Apr. 21, 2010 for European Patent Application No. 08169204.8, filed Oct. 7, 2003 (9 pages).

Yong, Li, et al., "A method for patterning multiple types of cells by using electrochemical desorption of self-assembled monolayers within microfluidic channels," Angewandte Chemie, 46(7):1094-1096, 2007.

Wang, L., et al., "An automatic and quantitative on-chip cell migration assay using self-assembled monolayers combined with real-time cellular impedance sensing," Lab on a Chip, 8(6):872-828, Jun. 2008.

Nie, et al., "On-chip cell migration assay using microfluidic channels," Biomaterials, Elsevier science publishers, 28 (27):4017-4022, Jul. 2007.

Jiang, X., et al., "Electrochemical desorption of self-assembled monolayers noninvasively releases patterned cells from geometrical confinements," Journal of the American Chemical Society, 125(9):2366-2367, Mar. 2003.

* cited by examiner

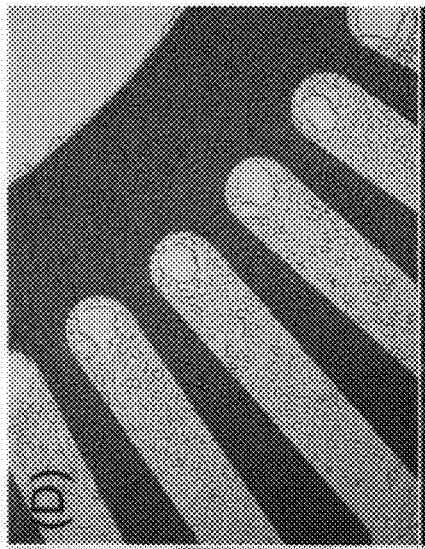
FIG. 5B  FIG. 5C  FIG. 5D
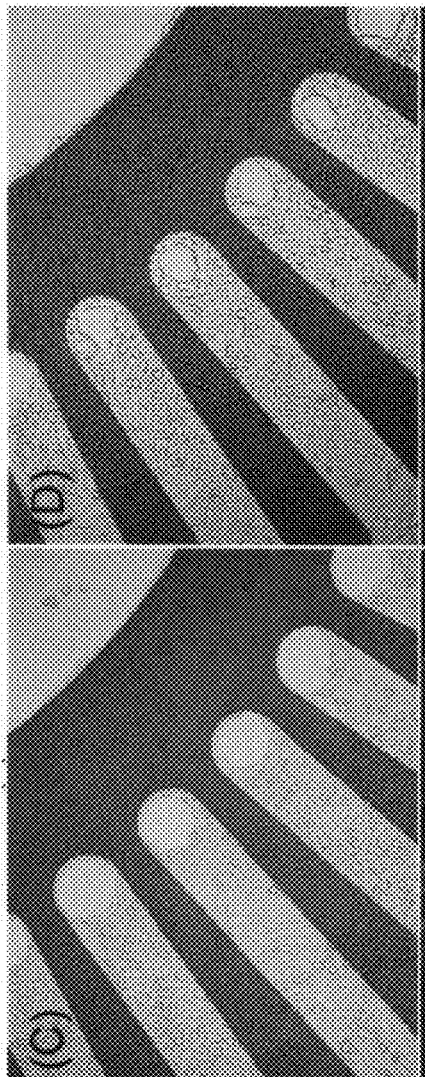
FIG. 5E
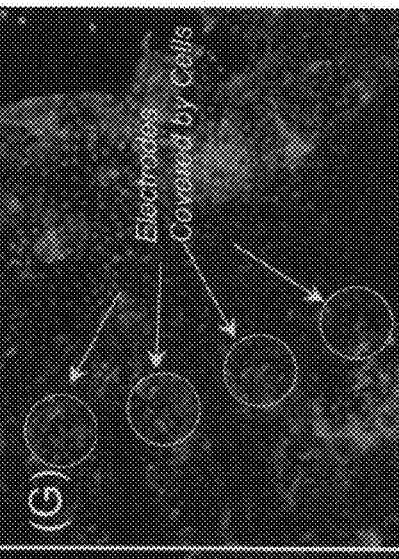
FIG. 5F
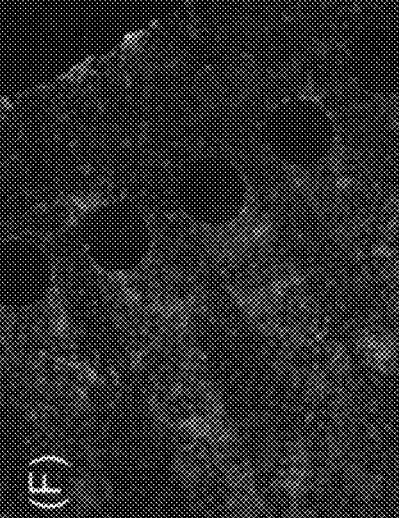
FIG. 5G

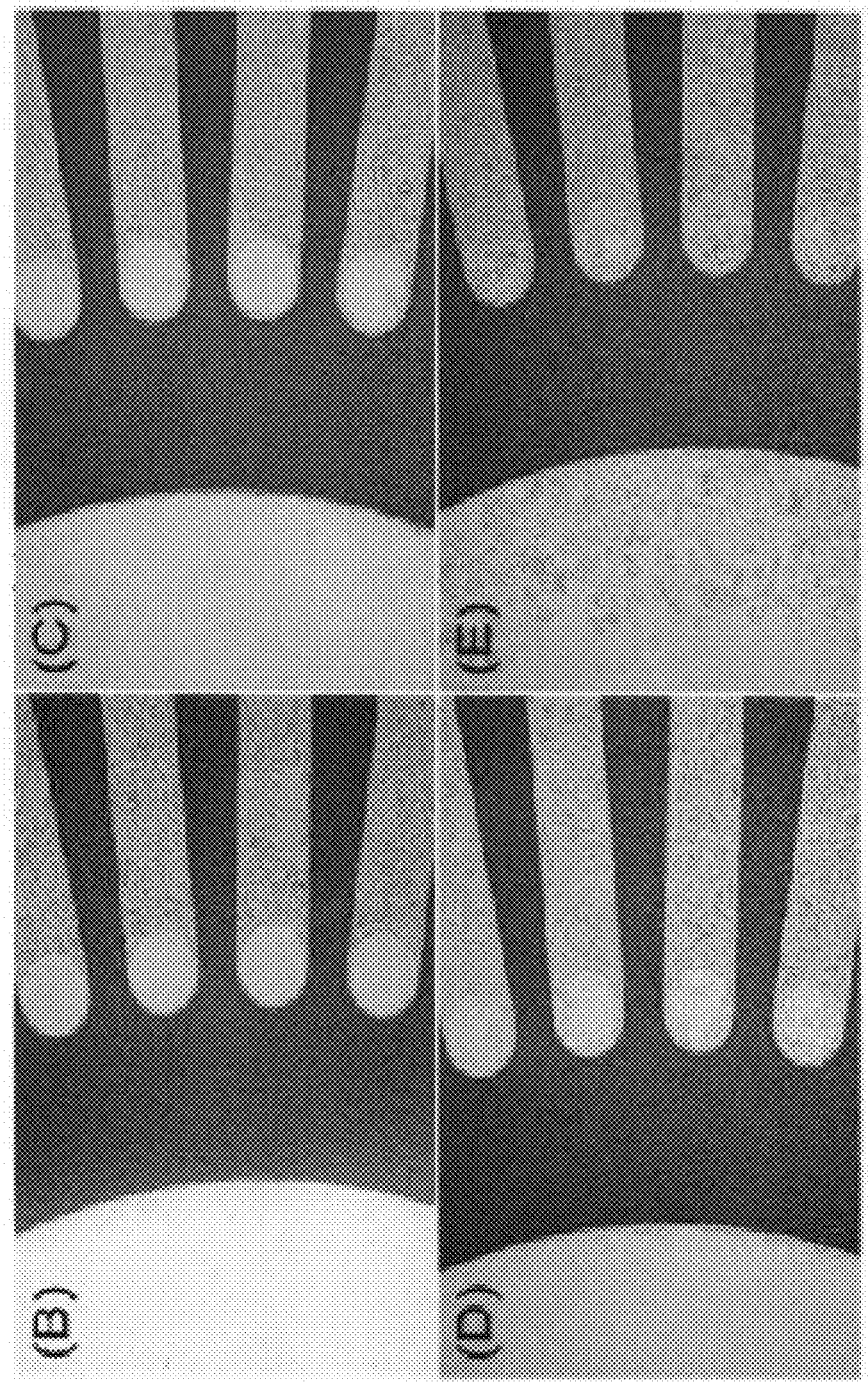

ON-CHIP CELL MIGRATION DETECTION

CLAIM OF PRIORITY

This application claims priority under 35 USC §119(a) to Chinese Patent Application No. CN 200810103526.7, filed on Apr. 8, 2008, the entire contents of which are hereby incorporated by reference.

BACKGROUND

Detection of cell migration is applicable in a variety of biological phenomena such as embryonic development, wound healing and immune response. In these and other applications, cell migration can be detected using various techniques. For example, in wound healing assay, a monolayer of cells are grown on a surface and a portion of cell monolayer is mechanically removed. Then, the scraped area is manually assessed by optical observation using microscopy.

SUMMARY

Techniques, systems and apparatus are described for detecting electrical impedance.

In one aspect, a microelectrode sensing device includes a substrate and an array of microelectrode sensors formed on the substrate. Each sensor includes at least one conductive layer formed above the substrate and patterned to include a counter electrode and multiple sensing electrodes to detect an electrical signal in absence and presence of one or more target cells positioned on at least a portion of a surface of each sensing electrode. The sensing electrodes are spaced apart and arranged around the counter electrode to provide a spatially averaged value of the detected electrical signal.

Implementations can optionally include one or more of the following features. The sensing electrodes can include multiple circular concentric sensing electrodes. The microelectrode sensing device can include one or more layers of insulating material formed between the sensing electrodes to electrically insulate the sensing electrodes from each another. The at least one conductive layer can be patterned to include the counter electrode and the sensing electrodes in a ratio of 1 counter electrode to N sensing electrodes, where N is a positive integer. The at least one conductive layer can be patterned to include the counter electrode and the sensing electrodes so as to provide a total surface area of the counter electrode that is at least twice a total surface area of the sensing electrodes. The at least one conductive layer can be patterned to include the counter electrode and the sensing electrodes to detect a change in the electrical signal in response to the one or more target cells migrating onto the surface of the plurality of sensing electrodes from an area outside of the surface of the sensing electrodes.

The at least one conductive layer can be patterned to include the counter electrode and the plurality of sensing electrodes to detect an impedance to a flow of the electrical signal in response to the one or more target cells migrating onto the surface of the sensing electrodes from an area outside of the surface of the sensing electrodes. The microelectrode sensing device can include a chemical coating applied on at least a portion of the surface of the sensing electrodes to inhibit adhesion of the one or more target cells onto the surface of the sensing electrodes. The chemical coating can include a self-assembled monolayer or bi-layer. The chemical coating can be made of a material that desorbs from the surface of the sensing electrodes in response to an electrical stimulus. The sensing electrodes can include sensing electrodes arranged to form a concentric shape around the counter electrode located at a center of the concentric shape. The sensing electrodes can be at an equal distance away from each other. Also, each sensing electrode can be at an equal radial distance away from a center of the counter electrode. The sensing electrodes can be symmetrical in shape and similarly sized to provide uniform impedance measurement from one electrode to another.

In another aspect, a system includes a microelectrode sensing device that includes a substrate, and an array of microelectrode sensors formed on the substrate, each sensor includes at least one conductive layer formed above the substrate and patterned to comprise a counter electrode and multiple sensing electrodes to detect an electrical signal in absence and presence of one or more target cells positioned on at least a portion of a surface of each sensing electrode. The sensing electrodes are spaced apart and arranged around the counter electrode to provide a spatially averaged value of the detected electrical signal. The system also includes an analysis system in communication with the microelectrode sensing device to receive from the microelectrode sensing device data representing at least the electrical signal detected by the sensing electrodes, and process the received data to obtain one or more impedance measurements.

Implementations can optionally include one or more of the following features. The analysis system can receive the data representing at least the electrical signal detected by the sensing electrodes in absence of the target cells to establish a control impedance measurement. The analysis system can receive in real-time, the data representing at least the electrical signal detected by the sensing electrodes over a period of time corresponding to migration of the one or more target cells onto the surface of the sensing electrodes from a location external to the surface. The analysis system can process the data received in absence of target cells and the data received over the period of time corresponding to migration of the one or more target cells to identify a change in impedance corresponding to the migration of the one or more target cells. The microelectrode sensing device can include a chemical coating on at least a portion of the surface of the plurality of sensing electrodes to inhibit adhesion of the one or more target cells onto the surface of the plurality of sensing electrodes. The chemical coating can include a self-assembled monolayer or bi-layer. The chemical coating can be made of a material that desorbs from the surface of the plurality of sensing electrodes in response to an electrical stimulus. The analysis system is configured to apply the electrical stimulus to the sensing electrodes to desorb the chemical coating.

In another aspect, a method for monitoring cell migration includes applying a chemical coating layer on at least a portion of a surface of each sensing electrode in a microelectrode sensing device that includes a counter electrode and sensing electrodes to inhibit adhesion of target cells on the surface of each sensing electrode. The target cells are seeded in the microelectrode sensing device to allow the seeded target cells to adhere to areas outside of the surface of each sensing electrode. An electrical signal is applied to each sensing electrode to desorb the applied chemical coating layer from the surface of each sensing electrode. A change is obtained in an electrical impedance measured by each sensing electrode in response to one or more of the seeded target cells migrating onto the surface of each sensing electrode.

Implementations can optionally include one or more of the following features. Applying the chemical coating can include applying a layer of thiol based compound. The chemical coating can be applied on a surface of the counter electrode in the microelectrode sensing device. Applying the chemical coating includes applying one or more self-assembled monolayers. A background impedance value can be measured before seeding the target cells. A normalized impedance value can be calculated based on the background impedance value. The change in the electrical impedance in real time can be monitored as the one or more of the seeded target cells migrate onto the surface of each sensing electrode until a steady state impedance is reached. Monitoring the change in the electrical impedance measured by each sensing electrode can include applying another electrical signal to each sensing electrode. Applying the other electrical signal can include in response to the other electrical signal applied to each sensing electrode, receiving a sensed signal from each sensing electrode and averaging the sensed signals to obtain an average impedance measurement due to the one or more of the seeded target cells migrate onto the surface of each sensing electrode.

In another aspect, a microelectrode sensing device includes a substrate means for providing a base layer. The microelectrode sensing device also includes an array of microelectrode sensing means for sensing electrical signals provided over the substrate. Each sensing means includes at least one conductive layer means for conducting electricity formed above the substrate and patterned to include a counter electrode means and multiple sensing electrode means to detect an electrical signal in absence and presence of one or more target cells positioned on at least a portion of a surface of each sensing electrode. The sensing electrode means are spaced apart and arranged around the counter electrode means to provide a spatially averaged value of the detected electrical signal.

Implementations can optionally include one or more of the following features. The sensing electrode means can include multiple circular or concentric sensing electrode means. The microelectrode sensing device can include one or more layers of insulating material means for insulating against electricity formed between the sensing electrode means to electrically insulate the sensing electrode means from each another. The at least one conductive layer means can be patterned to include the counter electrode means and the sensing electrode means in a ratio of 1 counter electrode means to N sensing electrode means, where N is a positive integer. The at least one conductive layer means can be patterned to include the counter electrode means and the sensing electrode means so as to provide a total surface area of the counter electrode means that is at least twice a total surface area of the sensing electrode means. The at least one conductive layer means can be patterned to include the counter electrode means and the sensing electrode means to detect a change in the electrical signal in response to the one or more target cells migrating onto the surface of the plurality of sensing electrode means from an area outside of the surface of the sensing electrode means.

The at least one conductive layer means can be patterned to include the counter electrode means and the plurality of sensing electrode means to detect an impedance to a flow of the electrical signal in response to the one or more target cells migrating onto the surface of the sensing electrode means from an area outside of the surface of the sensing electrode means. The microelectrode sensing device can include a chemical coating means for inhibiting cell adherence applied on at least a portion of the surface of the sensing electrode means to inhibit adhesion of the one or more target cells onto the surface of the sensing electrode means. The chemical coating means can include a self-assembled monolayer or bi-layer. The chemical coating can be made of a material that desorbs from the surface of the sensing electrode means in response to an electrical stimulus. The sensing electrode means can include sensing electrode means arranged to form a concentric shape around the counter electrode means located at a center of the concentric shape. The sensing electrode means can be at an equal distance away from each other. Also, each sensing electrode means can be at an equal radial distance away from a center of the counter electrode means. The sensing electrode means can be symmetrical in shape and similarly sized to provide uniform impedance measurement from one sensing electrode means to another.

In another aspect, a system includes a microelectrode sensing means that includes a substrate means for providing a base layer, and an array of microelectrode sensor means for providing signal sensing formed on the substrate. Each sensor means includes at least one conductive layer means formed above the substrate means and patterned to comprise a counter electrode means and multiple sensing electrode means to detect an electrical signal in absence and presence of one or more target cells positioned on at least a portion of a surface of each sensing electrode means. The sensing electrode means are spaced apart and arranged around the counter electrode means to provide a spatially averaged value of the detected electrical signal. The system also includes an analysis means in communication with the microelectrode sensing means to receive from the microelectrode sensing means data representing at least the electrical signal detected by the sensing electrode means, and process the received data to obtain one or more impedance measurements.

Implementations can optionally include one or more of the following features. The analysis means can receive the data representing at least the electrical signal detected by the sensing electrode means in absence of the target cells to establish a control impedance measurement. The analysis means can receive in real-time, the data representing at least the electrical signal detected by the sensing electrode means over a period of time corresponding to migration of the one or more target cells onto the surface of the sensing electrode means from a location external to the surface. The analysis means can process the data received in absence of target cells and the data received over the period of time corresponding to migration of the one or more target cells to identify a change in impedance corresponding to the migration of the one or more target cells. The microelectrode sensing means can include a chemical coating means for inhibiting cell adherence on at least a portion of the surface of the plurality of sensing electrode means to inhibit adhesion of the one or more target cells onto the surface of the plurality of sensing electrode means. The chemical coating means can include a self-assembled monolayer or bi-layer. The chemical coating can be made of a material that desorbs from the surface of the plurality of sensing electrodes in response to an electrical stimulus. The analysis means is configured to apply the electrical stimulus to the sensing electrode means to desorb the chemical coating means.

The described techniques, systems and apparatus may be implemented in various configurations and operated in ways that can provide one or more of the following advantages. For example, the described assay using surface treatment combined with cellular impedance measurement can be used to eliminate the need for physical removal of the cell monolayer, and thus can avoid damaging the cells near the wound edge. Because there are no (or only minimal) damaged cells in front of the migrating cells, the effect of the damaged cell in detection of the migrating cells can be avoid or minimized. For another example, the detection of cellular impedance can eliminate the time consuming and highly subjective nature of microscopic observation. In addition, the described techniques, systems and apparatus can be used for high-throughput research applications such as anti-migratory drug screening and drug discovery.

BRIEF DESCRIPTION OF THE DRAWINGS

FIGS. 5A-G illustrate an example application for monitoring cell migration.

FIGS. 8A-E show migration of fibroblast NIH-3T3 cells.

DETAILED DESCRIPTION OF THE DISCLOSURE

Figures 1A, 1B, 1C, 1D:
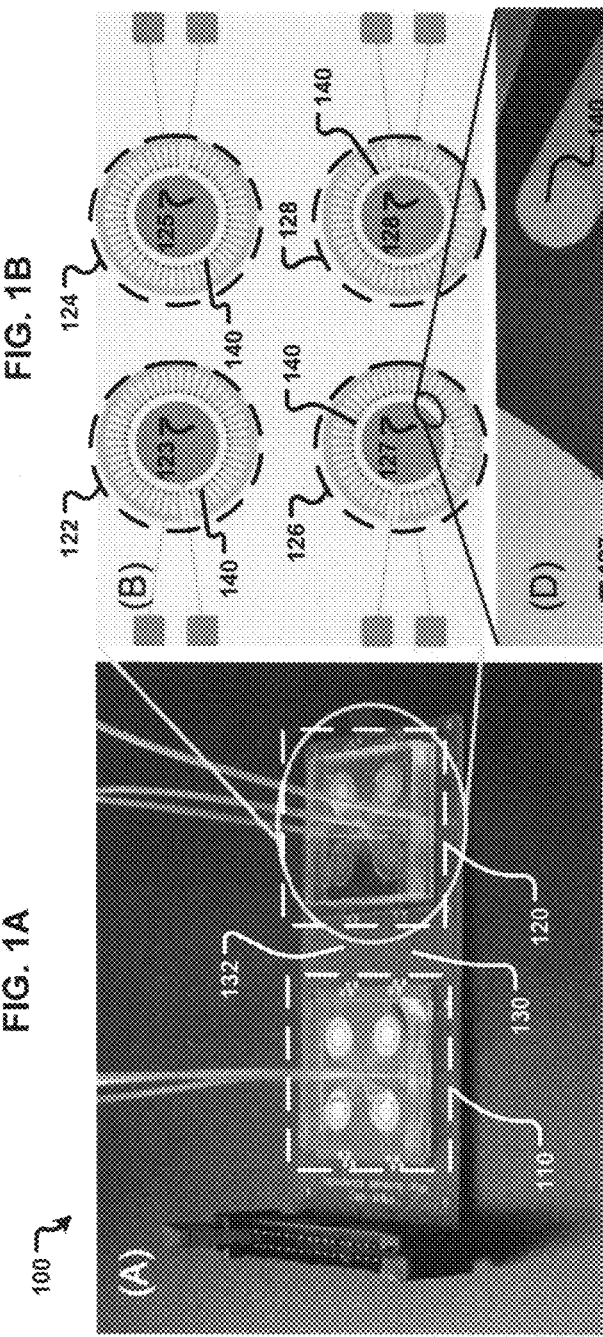
FIGS. 1A, 1B, 1C and 1D show an impedance sensing device for performing cell migration assay.

Detection of cell migration is applicable in a wide variety of biological applications such as embryonic development, wound healing and immune response. For example, due to a close relationship between cell migration and cancer metastasis, cell migration has been identified as a target for anti-cancer drug screening and cancer therapy. Cell migration can be detected using various techniques. For example, in wound healing assay, a monolayer of cells is grown on a surface and a portion of cell monolayer is mechanically removed. Recovery of the scraped area is assed by manual optical observation using microscopy. Physical removal of the cell monolayer could damage the cells near the wound edge. These possibly damaged cells in front of the migrating cells can affect the detected result of cell migration. Also, the detection methods based on microscopic can be subjective, time-consuming and strongly dependent on the investigators in determining the number of cells migrated. In addition, the manual and labor-intensive aspects associated with other detection methods may not be suitable for high-throughput research applications such as anti-migratory drug screening and drug discovery.

Examples of techniques, systems and apparatus are described below for on-chip detection of cell migration using surface treatment and cell impedance measurement. Various implementation techniques can be used to provide automatic impedance sensing for monitoring cell migration, and reliable quantitative measurements.

Surface Chemical Modification Using Self-Assembled Monolayers

A quantitative on-chip cell migration assay can be provided based on surface chemical modification using self-assembled monolayers (SAMs) and cellular impedance sensing. SAMs are used to form wound edges in a cell monolayer followed by cellular impedance sensing to monitor the whole process of cell migration in a real-time, automatic and quantitative manner. SAMs are types of various organic molecules that can align on a surface into two-dimensional, quasi-crystalline domains. SAMs of substituted alkanethiolates (R(C11-C15 alkylene)S—) adsorbed onto the surface of a gold film to inhibit cell adherence can be applied to pattern multiple types of cells within microfluidic channels. SAMs are applied on the surface of each electrode to inhibit cell adherence, forming blank areas in the confluence of a cell monolayer, which is used to mimic the wound in the wound healing migration assay.

To make the cell migration assay fully automatic and quantitative, the electrical cell-substrate impedance sensing (ECIS) technique is used to quantitatively monitor the progress of cell migration in real-time. ECIS. In ECIS, a weak probe AC electric signal is applied to the electrodes of an ECIS sensing device. When cells migrate and grow on the electrode, the cells physically impede the current resulting in an increase of impedance measured. Thus, ECIS can be used to monitor the process of cell migration. By combing the modified ECIS sensing device with the wound-forming SAMs technique, a real-time, high-throughput, quantitative cell migration monitoring is provided.

Sensor Chip Design

FIGS. 1A, 1B, 1C and 1D show an example sensor chip device for measuring cell impedance to detect cell migration. FIG. 1A shows a fully assembled device 100 that includes two sets 110 and 120 of electrode arrays. Each set of electrode arrays can be implemented in separate chips and then combined together as a single unit. Also, the two sets of electrode arrays can be implemented in a single chip. The two sets 110 and 120 of sensor arrays are connected together using one or more interconnects 130 and 132. Each set 110 and 120 of sensor arrays includes at least one microelectrode sensors, with each electrode sensor including one or more sensing electrodes and a counter electrode.

FIG. 1C shows a cross section view of an example sensor chip device. A sensing electrode 140 is disposed on a substrate 160. The electrode 140 is surrounded by insulating material 150. While FIG. 1C shows a single sensing electrode, the device 100 can be implemented using one or more sensing electrodes on a substrate, surrounded by insulating material. The insulating material 150 can be the substrate itself or an additional layer on the substrate 160. When two or more sensing electrodes 140 are implemented, each sensing electrode 140 is separated from each other by a gap of insulating material 150.

FIG. 1B shows examples of sensor arrays for measuring cell impedance. Each set of sensor arrays 110 and 120 include multiple sensors. For example, FIG. 1B shows four sensors 122, 124, 126, 128. The four sensors 122, 124, 126 and 128 represent four sensing units integrated in a sensing chip. However, each set of sensor arrays can include less than four sensors or more than four sensors. Each sensor 122, 124, 126, 128 includes multiple sensing electrodes 140 and a counter electrode 123, 125, 127 and 129. For example, the sensing electrodes 140 surround the counter electrode 127 in the sensor 126.

In FIG. 1B, the sensor 122, 124, 126, 128 are arranged as an optimized multi-island array structure. This multi-island array structure provides a reliable on-chip cell migration assay. In the example shown in FIG. 1B, each sensor 122, 124, 126, 128 includes 49 round sensing electrodes 140 and a counter electrode 127. Each sensing electrode 140 has a diameter of 200 μm, for example. The sensing electrodes 140 surround or encircle one counter electrode (e.g., 123, 125, 127 and 129) in the middle of the sensing electrodes. Each sensor 122, 124, 126, 128 can have a diameter of 4 mm, for example.

The sensing electrodes 140 can be positioned to form various geometric shapes around the centrally located counter electrode. For example, the sensing electrodes 140 can be arranged to form a circle that surrounds the centrally located counter electrode. Each sensing electrode 140 can be located at an equidistance from the centrally located counter. In additional, each sensing electrode 140 can be separated by equally spaced gaps of insulating materials. In addition to the circular or concentric shape, the sensing electrodes 140 can be arranged to form an oval shape, a square shape, a rectangle, a triangle, etc. to provide a spatially averaged electrical signal from the sensing electrodes 140.

FIG. 1D is an enlarged view of an example sensor. In FIG. 1D, one of the sensors (e.g., sensor 126) is enlarged to show 5 of the sensing electrodes 140 in the sensor 126. Each sensing electrode 140 is separated from the next sensing electrode 140 by a gap of insulating material 150 as described above. Also, the counter electrode 127 is shown to be separated from the sensing electrodes 140.

The multi-island array structure shown in FIG. 1A-1D can potentially provide one or more of the following advantages. For example, the multi-island array structure can provide a more uniform electric field which is beneficial for impedance sensing. Each sensing electrode 140 can generate an impedance signal regarding cell migration, so the signal obtained by the device 100 can be an average value for 49 independent repeating electrodes 140. Using the average value can reduce system error. Also, because the speed of cell migration may not be uniform among the 49 sensing electrodes, the 49 electrodes are arranged around the counter electrode 123, 125, 127 and 129 to produce a spatial average measurement of cell migration. This arrangement can improve the repeatability of the impedance measurement.

The example arrangement shown in FIGS. 1A-1D is provided for illustrated purposes only, and thus other arrangements of the electrodes can be used. In a simple implementation, the device 100 includes at least one sensing electrode and one or more counter electrodes. Other example arrangements include providing sensing and counter electrodes in ratios of at least 10:1, 20:1, 30:1, 40:1 or 50:1 sensing to counter electrodes.

In addition, the surface area of the counter electrode can designed to be several folds larger than the surface areas of the sensing electrodes. For example, the total counter electrode surface area can be at least 1, 2, 10, 20, 40, 80, 100, 200 or 500 times the total surface area of the sensing electrodes.

As shown in FIGS. 1A-1D, microfluidic chambers are fabricated to construct an environment for the cell culture and migration assay. The microfluidic chambers can be made of polydimethylsiloxane (PDMS) using a SU-8 technique. A mold can be created using SU-8 photoresist on a silicon wafer with a height of 100 μm, for example. Then, PDMS prepolymer solution (base+curing agent in a proportion of 10:1) is poured into the mold and cured in an oven at 72° C. for 2 hours to yield the elastomeric replicas containing the microfluidic chamber. The PDMS chamber can be bonded to the glass chip irreversibly after treatment with oxygen plasma generated by a plasma generator (FEMTO, Diener Plasma-Surface-Technology, Germany), and then assembled to the printed circuit board (PCB) by wire bonding. FIG. 1A above shows the assembled sensing device, which has a sandwich structure.

An example technique for fabricating cell culture cavity is described as follows. A cell culture cavity is fabricated using soft lithographic techniques. Briefly, polydimethylsiloxane (PDMS) is mixed with cross-linking agent in a proportion of 10:1, poured in the mold made of polymethylmethacrylate (PMMA) and cured in an oven at 72° C. for 3 hours to yield the elastomeric replicas containing the microfluidic channels for cell culture. On the end of each channel, a hole is created for entry of $CO_2$ throughout in the process of cell culture. A second hole in the middle of the cavity is created for cell seeding and for injection of the cell culture media.

The sensor chip is adhered to the print circuit board (PCB) using epoxy glue, each of the sensor electrodes is soldered to the printed circuit board for electrical connection, and then the PDMS cavity is bonded irreversibly to the sensor chip after treatment with oxygen plasma, forming the integrated cell culture and sensing device.

Figure 2:
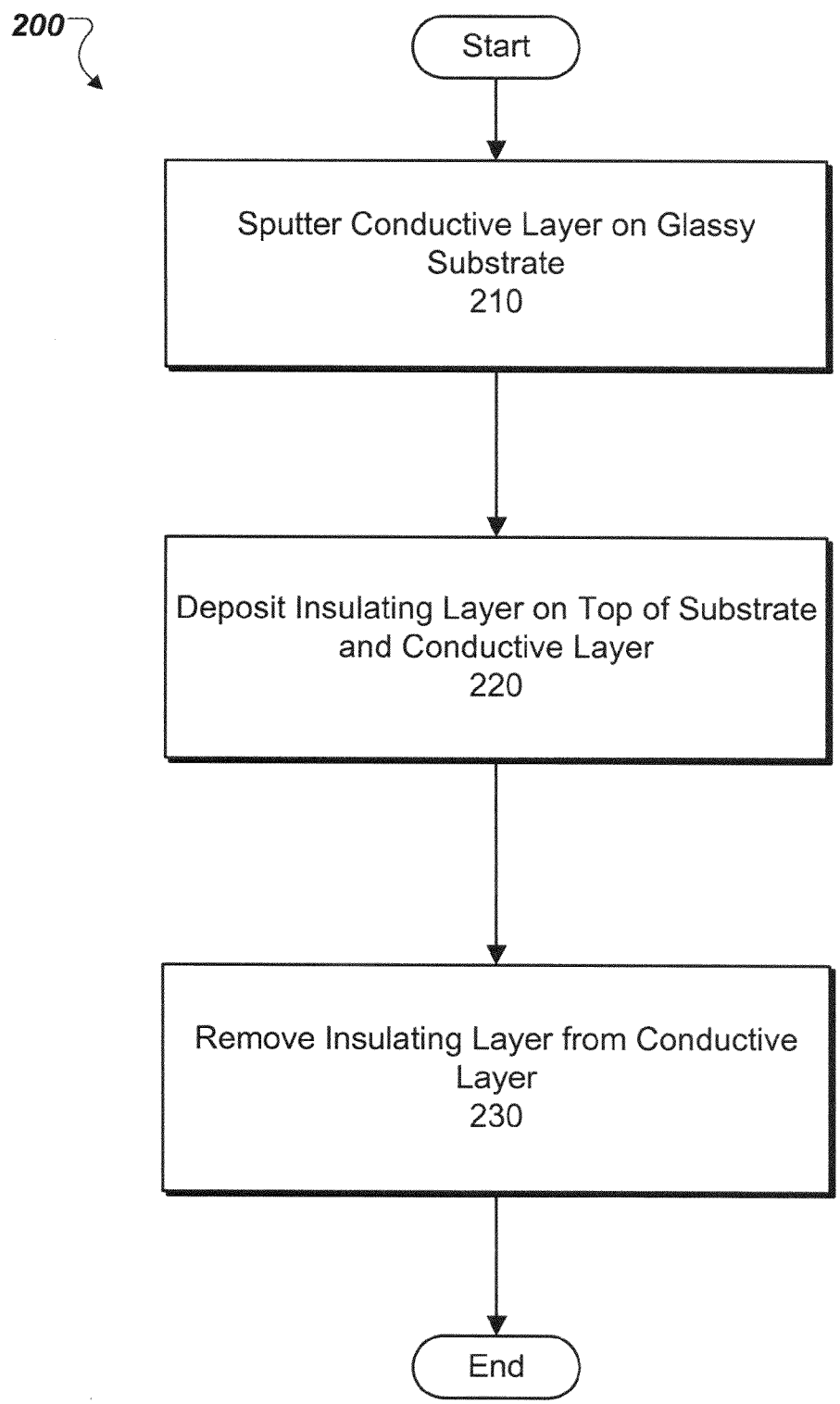
FIG. 2 shows an example process 200 for fabricating a device for measuring cell migration.

FIG. 2 shows an example process 200 for fabricating a device for measuring cell migration. A sensor chip device (e.g., device 100) is fabricated using standard semiconductor fabrication techniques. Briefly, a conductive layer of Au/Ti (Au 200 nm and Ti 20 nm) is sputtered on a glassy substrate, such as cleaned Pyrex glass wafer (210). The conductive layer forms the electrodes (sensing and counter) as described above with respect to FIGS. 1A-1D. The sensing electrodes 140 and counter electrodes 123, 125, 127 and 129 can be implemented using any conductive material or combination of conductive materials. In addition, the electrode surface can include a material on which a thiol SAM can form. Examples of electrode materials include gold, silver, copper, platinum, iridium, palladium, rhodium, mercury, osmium, ruthenium, gallium arsenide, indium phosphide, mercury cadmium telluride, graphite, conductive polymers and alloys or combination of these. While the example device 100 as described in this specification is produced using gold and/or platinum, the electrodes may be composed of more than one type of metal or alloy. Further, the sensing and counter electrodes can be composed of the same or different materials.

The surface of the substrate on which the electrodes contact should be non-conductive. Also, the substrate may take the form of a foil, a wafer or a chip of the desired material.

The substrate can include a layer or layers of a non-conductive material in contact with the surface of a substrate. The layers or layers of non-conductive material may be referred to as an insulation layer. Examples of an insulation layer include $SiO_2/Si_3N_4/SiO_2$. For example, an insulation layer of $SiO_2/Si_3N_4/SiO_2$ (400 nm/100 nm/500 nm) is deposited onto the substrate using plasma enhanced chemical vapor deposition (PECVD) (220). The insulation layer on the electrodes (conductive layer) and bonding pads are removed by reactive ion etching (230).

In some implementations, the impedance detection device as described in this specification can be fabricated using standard lift-off fabrication techniques. Pyrex glass wafer (e.g., from Corning, New York, 130 NY) is cleaned for about 15 minutes by the solution composed of $H_2SO_4$ and $H_2O_2$ (3:1 in volume ratio). The wafer is then washed with deionized water and dried with nitrogen gas. The wafer is coated with SPR6812 photoresist (e.g., from Rohm and Haas, Philadelphia, Pa.) and then soft-baked on a hot plate, for example at 95 for 2 min. The photoresist layer is exposed using EV620 (e.g., from EV Group, Austria), and the wafer is baked on a hot plate, for example at 110 for 3 min. After the formation of the patterned photoresist layer, a 30 nm thick Ti layer is sputtered on the wafer as an adhesion layer, followed by a 200 nm thick Au layer. The electrode pattern is defined by standard photolithographic processes and the wafer is soaked in acetone to remove photoresist and any redundant metal. Finally, the wafer with four independently integrated sensing chips is separated into four chips.

The chips are adhered to one Printed Circuit Board (PCB) by epoxy glue to form a sensing array. The electrodes are connected with the bonding pad on the PCB to make electrical connections with each sensing chip. The cell culture cavity of each chip is made from polydimethylsiloxane (PDMS) using soft lithographic techniques and was tightly bonded to the wafer by O2 plasma treatment. A flat polymethylmethacrylate (PMMA) plate is placed on the top of PDMS cavity as a lid during cell culture to maintain humidity and sterility.

Figure 3:
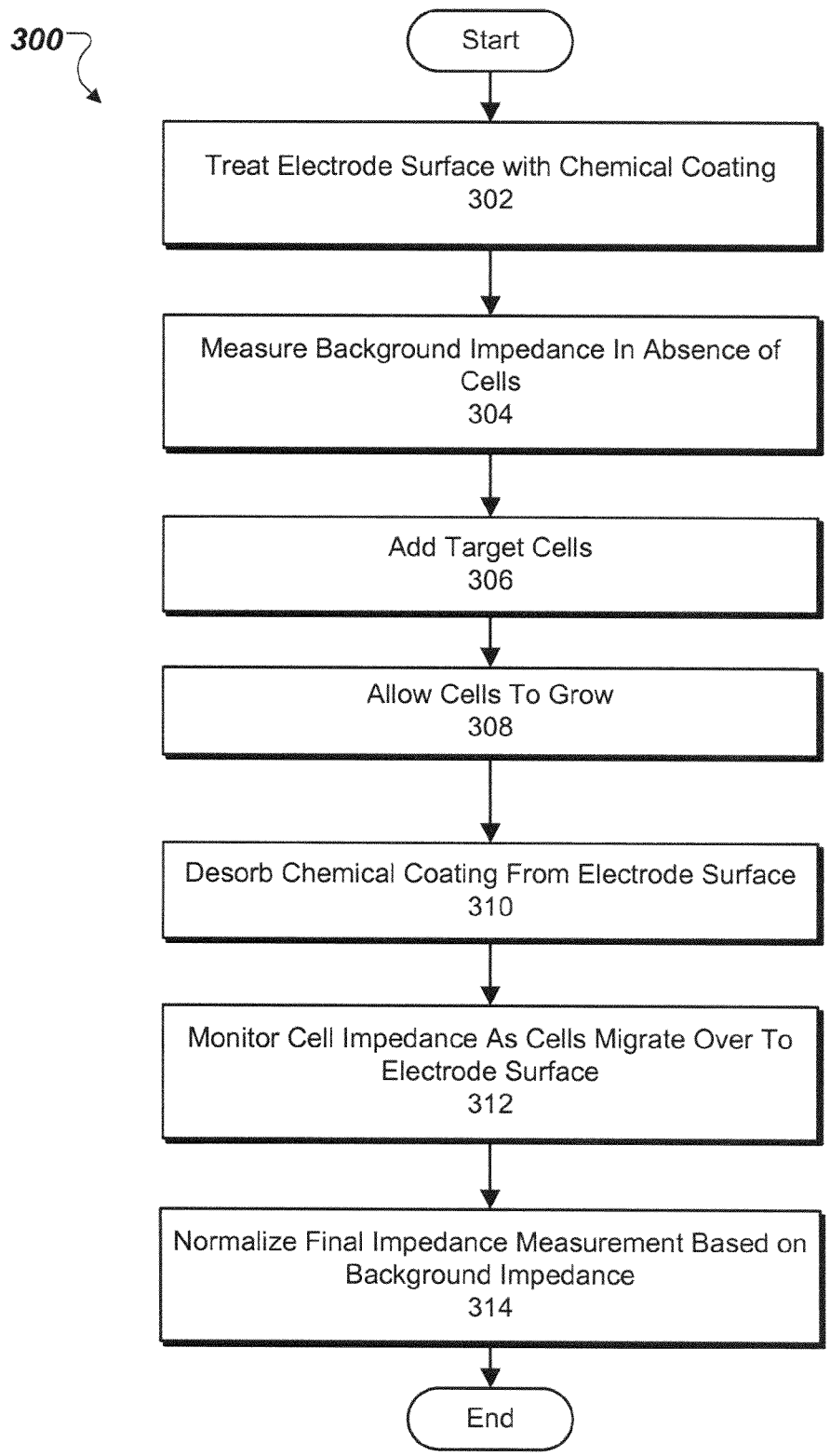
FIG. 3 shows an example process for measuring cell impedance.

FIG. 3 shows an example process 300 for measuring cell impedance. For at least one of the electrodes, the surface is treated with a chemical coating that inhibits cell adhesion onto the electrode (302). This generates a chemical coat-modified surface on the electrodes. The chemical coating maintains contact with the surface of the electrodes until desorbed by application of an electrical signal capable of desorbing the coating. The chemical coating can be applied by contacting the electrodes with a solution or suspension of coating material in a carrier, or by contacting the electrode with the coating material without a carrier. A background impedance value is measured in absence of cells (304). After measuring the background impedance (Z0), target cells are added to the device (306). A layer of cells is allowed to grow on the surface of the device (308). Because of the inhibition effect of the chemical coating-modified surface to cell adherence, the added cells do not adhere and grow on the surface of the electrodes. As a result, all the cells grow on the surface of the $SiO_2$ insulation substrate forming a cell monolayer. After incubation, wound edges are formed automatically on the device. Once the cells have grown over the surfaces, an electrical signal is applied to the electrodes, which causes the chemical coating to desorb from the electrodes (310). This provides a cell-free electrode surface surrounded by cells growing on the adjacent insulation. The cell impedance ($Z_x$) is monitored in real-time as the cells grow or migrate across the electrodes (312). Cells growing on the electrodes can cause measurable changes in the electrical properties of the circuit, e.g., impedance; consequently, the rate of cell migration or spreading can be monitored by monitoring electrical properties of the electrodes. The final impedance data is normalized as $Z_x/Z_0$ (314). The normalized impedance data reflects the impedance variation induced by the attachment of the cells.

Example Protocol Using SAMs

For illustrative purposes, the process 300 is described using an example protocol for monitoring cell migration. An example protocol includes preparing an impedance measuring device (e.g., device 100) for impedance measurement by sterilizing the device. After sterilization, (e.g., in 75% ethanol for 20 minutes and then exposure to UV irradiation for another 30 minutes), a thiol compound is added to the microfluidic cavities. Thiol compound $(HS(CH_2)_{11}(OCH_2CH_2)_6OH$ (abbreviated as "EG6") is obtained from Sigma-Aldrich (St. Louis, Mo.). EG6 (1.5 mM in ethanol) can be added to each microfluidic cavity of the device using a syringe and incubated for 8 hours at room temperature. Then, the microfluidic cavities are washed by ethanol followed by PBS buffer. Before cell seeding, tissue culture media is injected into chambers of the device to read the background impedance value ($Z_0$).

After measuring the background impedance ($Z_0$), suspension cells (e.g., $2 \times 10^5$ cells $cm^{-2}$) are added to the microfluidic cavities. The device is placed into an incubator for the cell culture and migration assay. The SAMs are desorbed from the electrode surface by applying a stimulus signal. For example, a DC current (provided by an ordinary DC power supply) can be imposed on the electrodes with an amplitude of 1.5 V for 30 seconds. The gold electrodes of the device serves as the cathode, while platinum wire immersed in the culture media serves as the anode.

At the same time, the impedance ($Z_x$) is measured in real-time with a time resolution of 5 minutes, for example. The time resolution can be increased to about 5 seconds per measurement. The final impedance data is normalized as $Z_x/Z_0$ (310). The normalized impedance data reflects the impedance variation induced by the attachment of the cells.

For impedance sensing, an AC probe sine signal is applied to the electrodes of the device. When cells attach and spread on the surface of sensor electrodes, the cells inhibit the current resulting in a variation of the impedance. Measurements can be carried out using a multifunctional data acquisition card NI DAQ PCI-6110 (National Instruments, Austin, Tex.) controlled by a LabVIEW® (National Instruments) program, for example. The impedance is calculated, recorded and displayed automatically in real time.

Surface Treatment with Chemical Coating

As described above, the chemical coating applied to the electrode surface is assembled on the surface of the electrode and not on the surface of the substrate and the surface surrounding the electrode does not have the chemical coating. In addition, the coating inhibits cell adherence onto the electrode. Further, the coating can be desorbed from the electrode upon application of an electrical signal to the electrode.

The chemical coating applied to the electrode surface can include a SAM. Such coating layer is self-assembled because the layer assembles automatically due to attractive forces between the electrode and the coating material. A monolayer is produced because the coating must include functional groups that attach to the electrode material. Self-assembled monolayers can be prepared, for example, simply by adding a solution of the desired molecule onto the substrate surface and washing off the excess.

The monolayer may be formed from a precursor solution or mixture that contains a precursor substance, selected on the basis of coordination chemistry with respect to the precursor and the surface to be coated. As a non-limiting example of coordination chemistry, when the surface to be coated includes aluminum, suitable precursors are n-alkanoic acid, alkyl oxalic acid, hydroxamic acid, phosphonic acid, or sulfate. Coordination can be provided between the surface of a gold or platinum with a coating of a thiol, phosphorus or arsenic containing compound. Details of coordination chemistry can be found in U.S. Pat. No. 5,523,878, contents of which are incorporated by reference as a part of this specification.

In addition, the coating of the cell migration device can include a mono- (one molecule thick) or bi- (two molecules thick) layer, or a mixture of a mono- and bi-layer. Other examples include a coating composed of a multi-layer (more than two molecules thick). Also, the coating may include well-ordered molecules or randomly distributed molecules.

The coating can selectively maintain contact with the surface of the electrode and not the surface of the substrate. For example, an attractive force between the coating and the surface of the electrode can maintain contact between the coating and the electrode surface. Absence of such attractive force between the coating and the surface of the surrounding substrate or insulation material can prevent application of the coating on the substrate and the insulation layer. Examples of attractive forces include intermolecular forces, such as electrostatic, ionic, van der Waals, H-bonding, covalent bonds, and dipole-dipole interactions.

The chemical coating can cover various portions of the electrode surface. For example, the coating can cover at least 75%, 85%, 95%, or 98% of the surface of the electrode. Also, the coating can include a confluent layer that completely covers the surface of the electrode.

The coating can prevent ells from contacting or adhering to the surface of the electrode until desorbed from the electrode surface. For example, the coating can remain on the electrode surface until the electrodes are stimulated with an electrical impulse capable of desorbing the coating. The electrical impulse can be characterized by a certain voltage and time applied to the electrode, which is sufficient to desorb all or substantially all of the coating material.

The coating as described in this specification can be generated using a thiol containing molecule. The thiol containing molecule adsorbs through the sulfur (SH) head group to the substrate surface. The thiol containing molecule can include a hydrocarbon chain that extends from the surface of the substrate and results in densely packed monolayer films. Descriptions of a thiol containing compound can be found in U.S. Pat. No. 5,514,501, the contents of which are incorporated by reference as a part of this specification.

Other types of compounds that can produce alkylthiolate monolayers include dialkyl sulfides and dialkyl disulfides. Dialkyl sulfides correspond to the general formula $R(CH_2)_mS(CH_2)_nR$, and is optionally substituted. Either symmetrical or asymmetrical dialkyl sulfides may be used. Examples of symmetrical dialkyl sulfides include $[CH_3(CH_2)]_2S$, $[HOOC(CH_2)_n]_2S$, and $[F(CF_2)_m(CH_2)]_2S$, each of which may be optionally substituted. Examples of asymmetrical dialkyl sulfides include $CH_3(CH_2)_9S(CH_2)_{10}COOH$, $CH_3(CH_2)_5S(CH_2)_{10}COONa$ and $CH_3(CH_2)_{15}S(CH_2)_{15}COOH$, each of which may be optionally substituted. Examples of dialkyl disulfide compounds include symmetrical dialkyl disulfides such as $[S(CH_2)_nOH]_2$, $[S(CH_2)_nCH_3]_2$, $[S(CH_2)_nBr]_2$, and $[S(CH_2)_nCOOH]_2$, each of which may be optionally substituted. Asymmetrical dialkyl disulfides may correspond to the formula $R(CH_2)_mS—S(CH_2)_nR$, which may be optionally substituted. Each m and n is independently selected from an integer from 0-21. Each R is independently selected from a group consisting of H, C1-C20 alkyl, OC1-C20 alkyl, OH, HOOC, $NH_2$, $CF_3$, and halogen. Halogen is defined as bromine, chlorine, iodine, or fluorine. In some embodiments, the group R includes any functional group that can confer a desired character on the SAM, depending on the intended use. Additional compounds that can form a coating include unsaturated and/or fluorinated versions of the foregoing examples and formulas.

Optional substituents may include C1-C8 alkyl, C1-C8 alkenyl, C1-C8 alkynyl, C1-C8 heteroalkyl, halo, CN, COOR, =O, =NR, =NOR, =N—CN, OR, or $NR_2$, wherein each R is independently H, C1-C6 alkyl, or C1-C6 heteroalkyl, and wherein two R can optionally cyclize to form a 3-7 membered ring containing 0-2 heteroatoms selected from N, O and S.

Alkylene as used herein refers to a divalent hydrocarbyl group. Typically it refers to —$(CH_2)_n$— where n is 1-21. An alkylene can also be substituted by other groups, branched, or of other lengths, and the open valences need not be at opposite ends of a chain. Thus, —CH(Me)— and —C(Me)$_2$- may also be referred to as alkylenes, as can a cyclic group such as cyclopropan-1,1-diyl.

Cell Seeding on the Migration Detection Device

Various techniques can be used to introduce cells onto the cell migration detecting device described in this specification. For example, CaSki, HeLa, Vero-E6 and NIH-3T3 cell lines are obtained from the American Type Culture Collection (ATCC, Manassas, Va.). These cells are incubated at 37° C. in a humidified incubator containing 5% $CO_2$ atmosphere. HeLa and Vero-E6 cell lines are incubated with Dulbecco's modified Eagle's medium supplemented with 10% fetal bovine serum. CaSki cell line was maintained with RPMI-1640 media supplemented with 10% fetal bovine serum while NIH-3T3 cell line was incubated with Dulbecco's modified Eagle's medium supplemented with 10% bovine calf serum. For seeding cells onto the sensors, a monodisperse cell suspension is prepared using standard tissue culture techniques with 0.25% trypsin containing 0.53 mM EDTA.

Figure 4A:
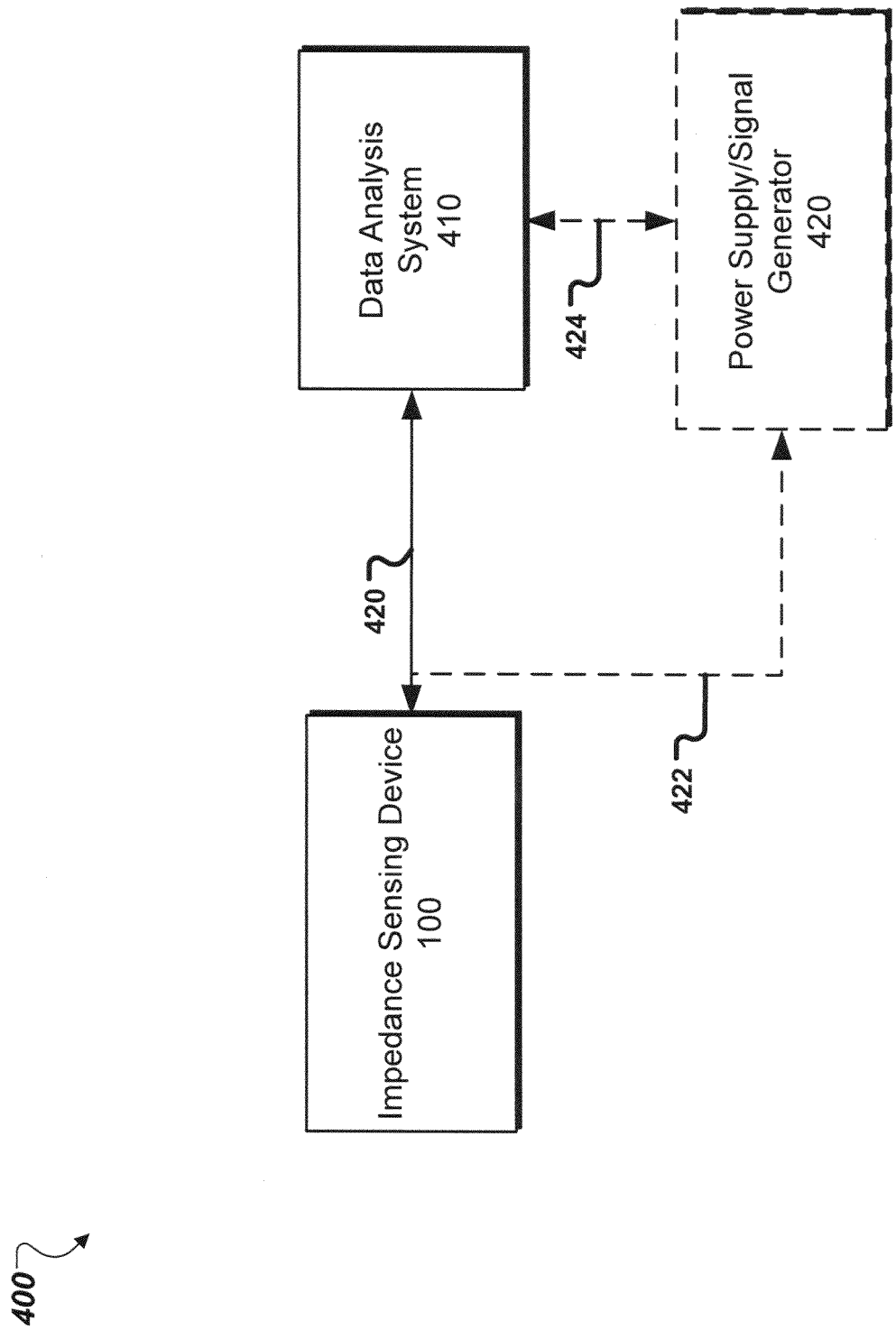
FIGS. 4A, 4B and 4C show examples of a system for monitoring cell migration.
Figure 4B:
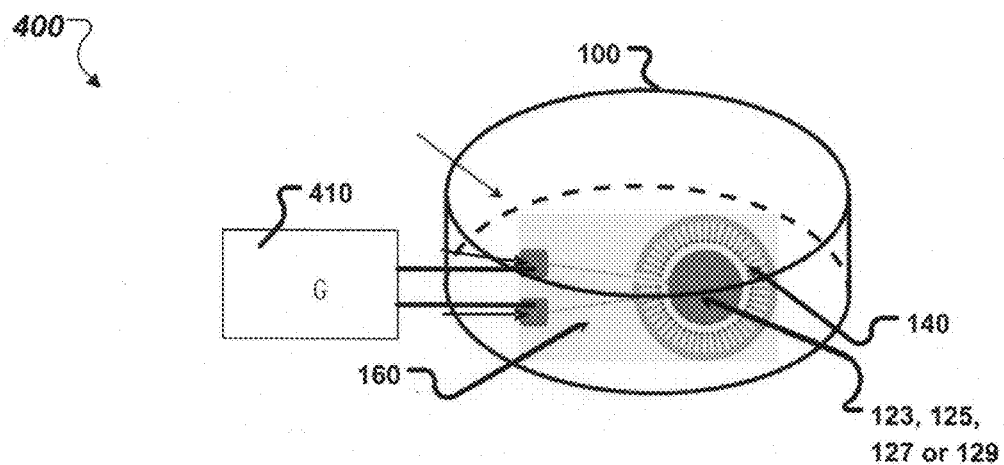
Figure 4C:
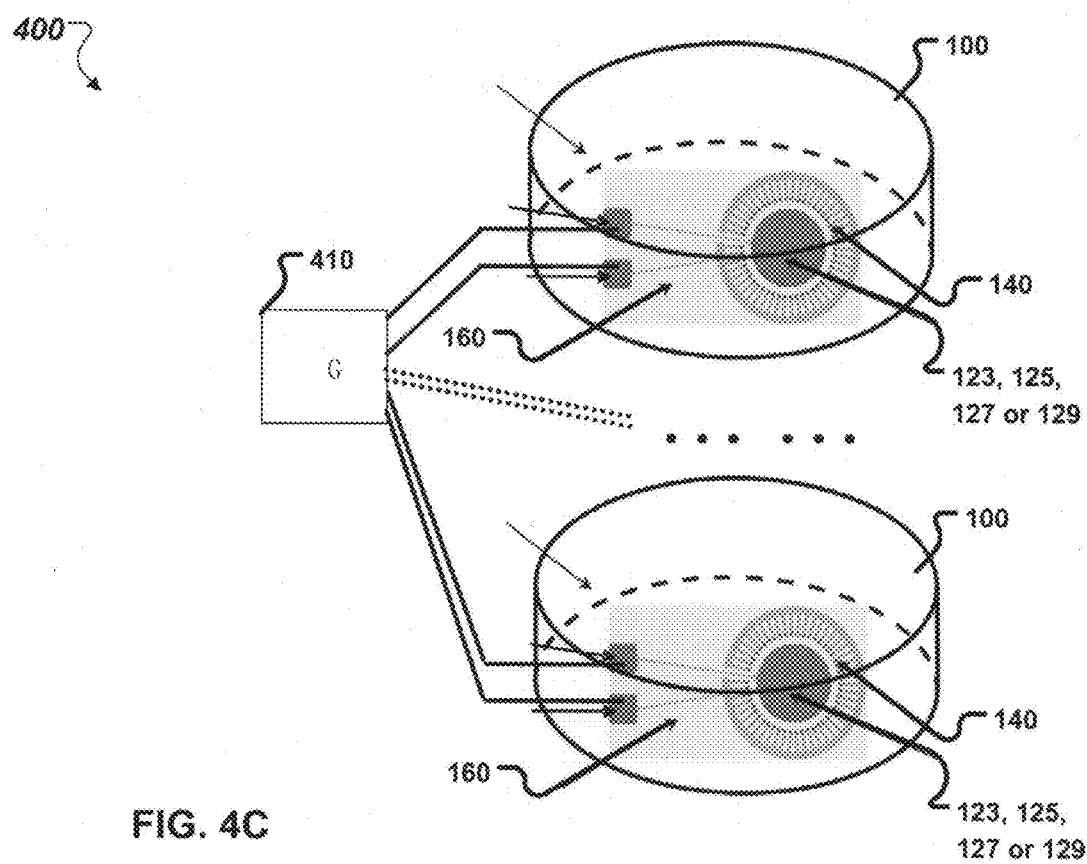

FIGS. 4A, 4B and 4C show examples of a system 400 for monitoring cell migration. As shown in FIG. 4A, the system 400 includes an impedance sensing device 100 in communication with an data analysis system 410 over a bidirectional communication link 420. The impedance sensing device 100 can send an output signal that includes cell impedance data measured from the sensing electrodes 140 in the impedance sensing device. The data analysis system 410 processes the output signal received from the data analysis system 410 to determine the final impedance data in real-time. For example, signals from the 49 sensing electrodes 140 shown in FIGS. 1A-1D above can be averaged to obtain an averaged impedance measurement. The data analysis system 410 can normalize the average data against the background impedance measurement.

The data analysis device 410 includes an instrument capable of measuring at least one electrical property. For example, the data analysis system 410 can process the output data from the impedance sensing device 100 to measure electrical properties, such as impedance, resistance, capacitance, inductance and frequency. Examples of an instrument that measures impedance include a LCR meter (L is inductance, C is capacitance and R is resistance or impedance). In addition, the data analysis system 410 can be implemented using one or more data processing devices, such as a desktop computer, a server computer, a portable computer, etc. While FIG. 4A shows only one impedance sensing device 100 in communication with the data analysis system, 410, the analysis device 410 is designed to interface with more than one sensing devices 100.

In addition, the data analysis system 410 can generate an electrical signal to desorb the coating on the surface of the electrodes. The generated electrical signal can be transmitted to the impedance sensing device 100 over the bidirectional communication link 420 to desorb the coating on the surface of the electrodes in the impedance sensing device 100.

The system 400 can optionally include a power supply/signal generator 420 in communication with the impedance sensing device 100 and/or data analysis system 410 over bidirectional links 422 and/or 424. Instead of the data analysis system 410, the power supply/signal generator 420 can generate the electrical signal to desorb the coating from the surface of the electrodes. The power supply/signal generator sends the generated signal to the impedance sensing device 100 to desorb the coating layer.

FIG. 4B shows another example of the system 400 for detecting cell migration. In this example, a single device 100 is connected to an analysis system 410. The device 100 includes gold electrodes 140 fabricated on a glass substrate 160. The gold electrodes 140 surround a counter electrode 123, 125, 127 or 129. The substrate 160 is adhered onto the bottom of a container 412, such as a petri dish for cell culture.

FIG. 4C shows yet another example of the system 400 for detecting cell migration. In this example, multiple devices 100 are connected to the analysis system 410 that measures at least one electrical parameter, e.g., impedance, resistance, capacitance, inductance or frequency.

In addition, the data analysis system 410 can control the sensing device 100 to monitor the impedance measured by the electrodes in real time. For example, the data analysis system 410 can control the sensing device 100 to measure a control impedance measurement in absence of cells on the surface of the electrodes. Then, the data analysis system 410 can generate and apply an electrical signal to desorb the coating on the surface of the electrodes. After desorbing the coating, cells will begin to migrate onto the surface of the electrodes. The data analysis system 410 can measure the transient impedance at the electrodes as the cells migrate on the surface of the electrodes. This can be achieved by performing real-time monitoring of the impedance after desorbing the coating. The change in impedance measurement as the cells migrate onto the surface of the electrode can be processed and analyzed to determine the effects of cell migration on the impedance value.

Example Application

CaSki Cell Migration

Figure 5A:
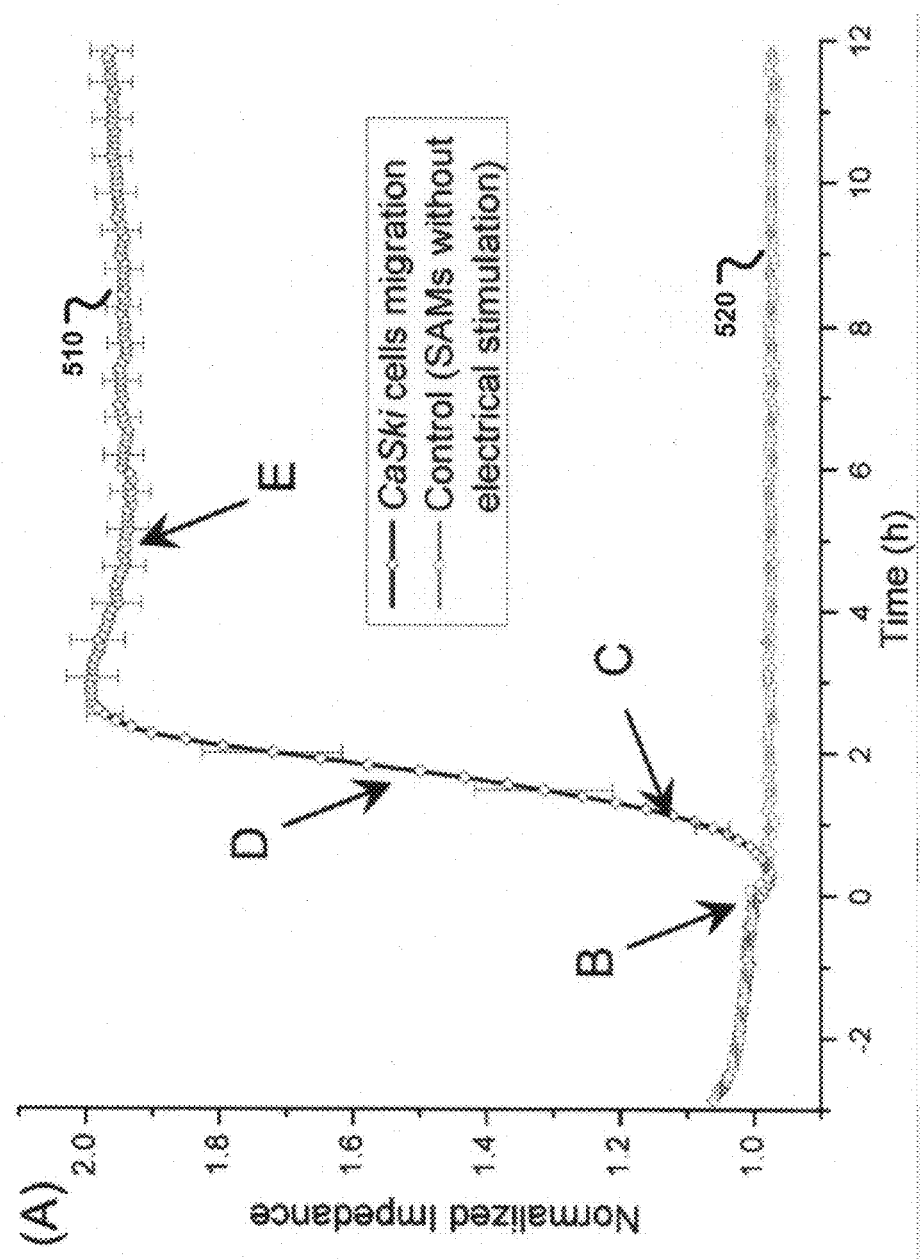

FIGS. 5A-G illustrate an example of monitoring of cell migration. FIG. 5A shows measured impedance variation for CaSki cells, showing the real-time progress of cell migration. FIGS. 5B-E show example photographs taken in the progress of cell migration onto the electrodes. FIGS. 5F-G show examples fluorescence images of a sensor, showing cell viability after modification of the SAMs and application of the DC current. In order to evaluate the potential influence to the cell viability, especially to the cells on the edges of the electrodes, fluorescence dyes calcein-AM and PI is used to label cells and test their viability. Healthy cells present a green fluorescence while dead cells presents a red fluorescence.

The example cell migration shown in FIGS. 5A-G presents data demonstrating that exemplary devices, systems and techniques described in this specification are effective in providing an artificial wound edge formation, subsequent cell migration monitoring, and cell viability detection.

FIG. 5B shows that because of the inhibition effect of the SAM-modified gold surface to cell adherence, cells could not adhere and grow on the surface of the gold electrodes treated with a chemical coating. As a result, all the cells grew on the surface of the $SiO_2$ insulation substrate forming a cell monolayer. After incubation for 24 hours, wound edges are formed automatically on the chip as is shown in FIG. 5B.

Once the wound edges in cell monolayer are formed, a 1.5 V DC current is applied to the electrodes for 30 seconds. The SAMs were desorbed from the gold electrodes due to the applied current. With the inhibitory coating gone, the cells start to migrate onto the electrodes, and the progress of cell migration is monitored by the impedance sensing in real-time.

FIG. 5A shows example impedance data measured for CaSki cell migration on the electrodes after applying an electrical stimulus to remove the SAMs from the electrode surface (510). For example, in response to an application of the electrical stimulus that includes a DC current applied at a time of 0 hour, the impedance value increases gradually until leveling off. The sharp rise in impedance after the application of a DC current to desorb EG6 from the electrodes indicates cell migration onto the electrodes. The time at which the DC current is applied is marked as 'B' and corresponds to FIG. 5B. The other time points marked 'C', 'D', and 'E' correspond to FIGS. 5C, 5D and 5E. The impedance data as shown on the y-axis represents normalized impedance ($Z_x/Z_0$) values. The X-axis represents time in hours.

In FIG. 5B, wound edges are shown where the chemical coating, such as the thiol compound EG6 is still present on the surface of the electrodes. The chemical coating prevents cells from migrating onto the EG6 coating treated electrode surface. When the DC current is applied, the EG6 coating is desorbed from the electrode surface and the cells begin to migrate onto the EG6-free electrode surface as shown in FIG. 5C. At time point D, even more cells have migrated onto the electrode surface as shown in FIG. 5D. At time point E, the electrode surface is nearly completely covered by migrating cells as shown in FIG. 5E. This corresponds to the impedance measurements that levels off after the initial rise as shown in FIG. 5A at time E. Thus, these microscopic photographs validate the relationship between impedance variation and cell migration.

Referring back to FIG. 5A, the impedance data shown for control essays (520) are measured without application of a DC current, and thus the SAMs are retained on the electrode surface. In contrast to the application of the DC current, the normalized impedance value for the control assays does not change over time because in absence of the DC current, the SAMs are retained on the electrode surface. Thus, the control assays show little evidence of cell migration onto the electrodes.

After the DC current is applied to the electrodes, calcein-AM combined with PI is used to test the influence of the DC current upon the viability of the cells. The experimental result is shown in FIG. 5F, a fluorescence image of the sensor soon after the application of the DC current. In FIG. 5F, the cells growing near the edges of the electrodes present a bright green fluorescence without any red color. Red colored cells represent the dead cells. This lack of red color in the cells shows that the applied DC current do not significantly affect the cells adjacent to the electrodes.

After the DC current effectively desorbed the SAMs from the gold electrodes, the influence of the modified electrodes upon cell viability is evaluated using fluorescence dyes. FIG. 5G shows an experimental fluorescence image of the sensor after the application of the DC current and sufficient time has passed for the cells to migrate onto the electrode surface. FIG. 5G shows that the cells that have migrated and grown on the round electrodes presented the same bright green fluorescence as the cells that are far away from the electrodes. FIG. 5G shows little or no red colored cells representing the dead cells.

Example Application

Quantitative Comparison of the Migration Speed of Mammalian Cells in Real-Time

Figure 6A:
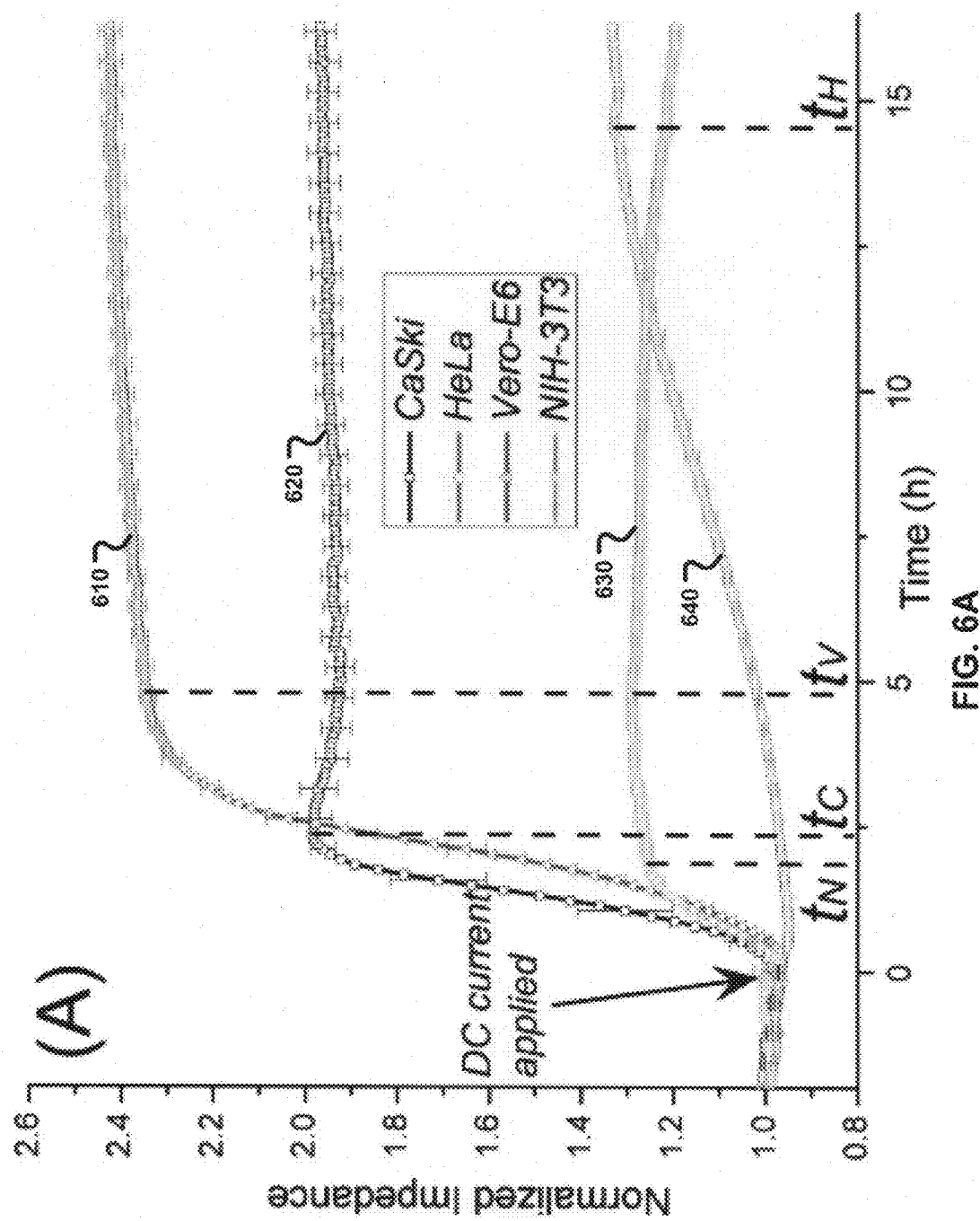
FIGS. 6A, 6B, 6C and 6D show monitored impedance variation for cell migration and cell proliferation.
Figure 6B:
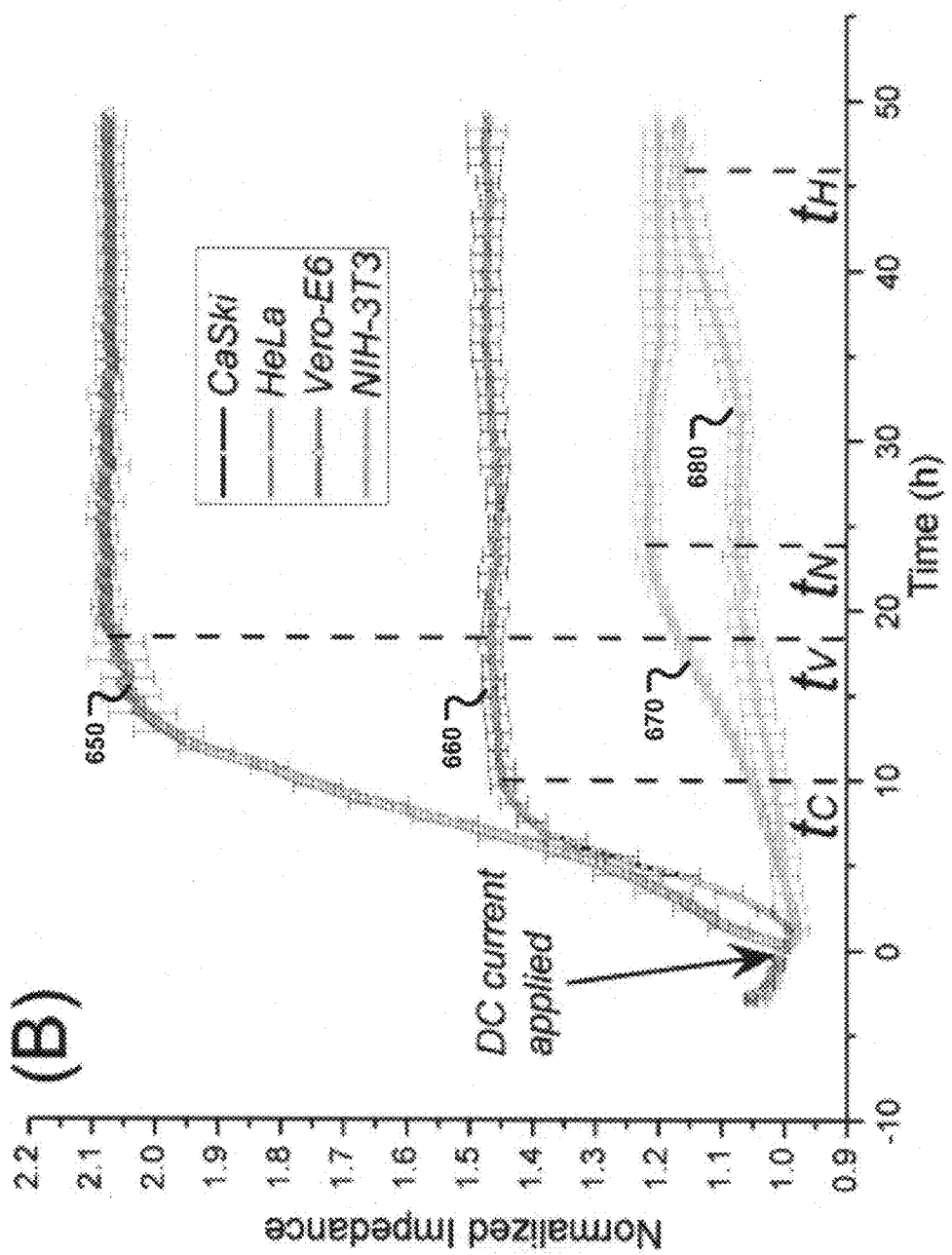

The cell migration detection devices, techniques and systems described in this specification can be used to effectively quantify and compare the migration speed of cells in real time. For example, using an on-chip cell migration assay, migration of four types of cell lines (CaSki, HeLa, Vero-E6 and NIH-3T3) is monitored in parallel, and the migration speed is measured in real-time. The cells proliferate in the presence of their associated serums, but do not proliferate without the serums. Two groups are prepared: (1) Culture media with 10% serum, where cells can proliferate on the sensing electrodes and cell migration combined with cell proliferation can be detected; (2) Cells starved in serum-free culture media for 12 hours before growing in the serum-free medium, where the cell proliferation independent cell migration can be monitored. FIGS. 6A and 6B show monitored impedance variation for above identified groups (1) and (2) respectively. For example, FIG. 6A shows the measured impedance signals for CaSki 620, HeLa 640, Vero-E6 610 and NIH-3T3 630 for group (1). FIG. 6B shows the measured impedance signals for CaSki 660, HeLa 680, Vero-E6 650 and NIH-3T3 670 for group (2).

In FIGS. 6A and 6B, after a DC current is applied and SAMs are desorbed from the electrodes, the impedance value starts to increase in different patterns for the four types of cells. As the cells migrate onto the sensing electrodes, the impedance value increases until all of the sensing electrodes are entirely covered by the cells. This indicates a saturation of the impedance signals.

Figure 6D:
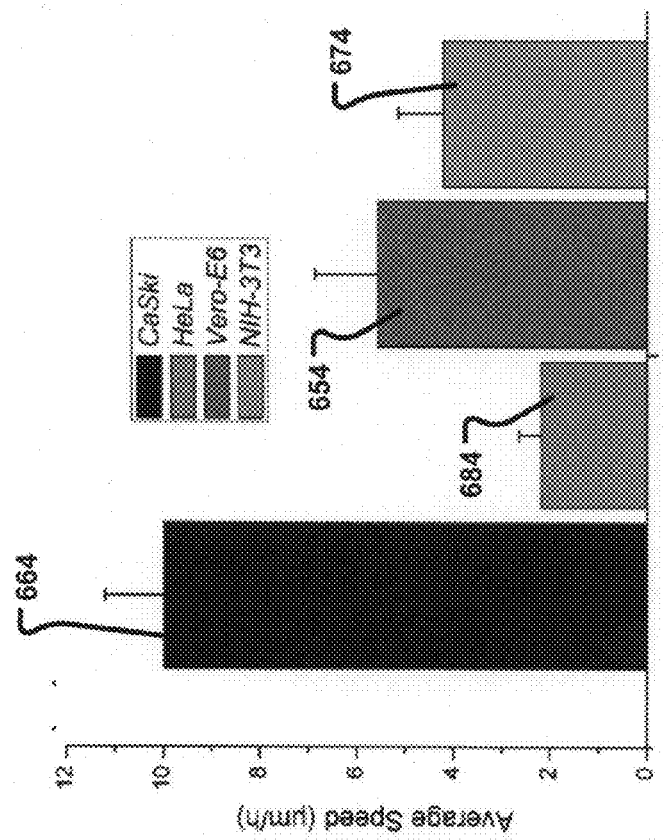
Figure 6C:
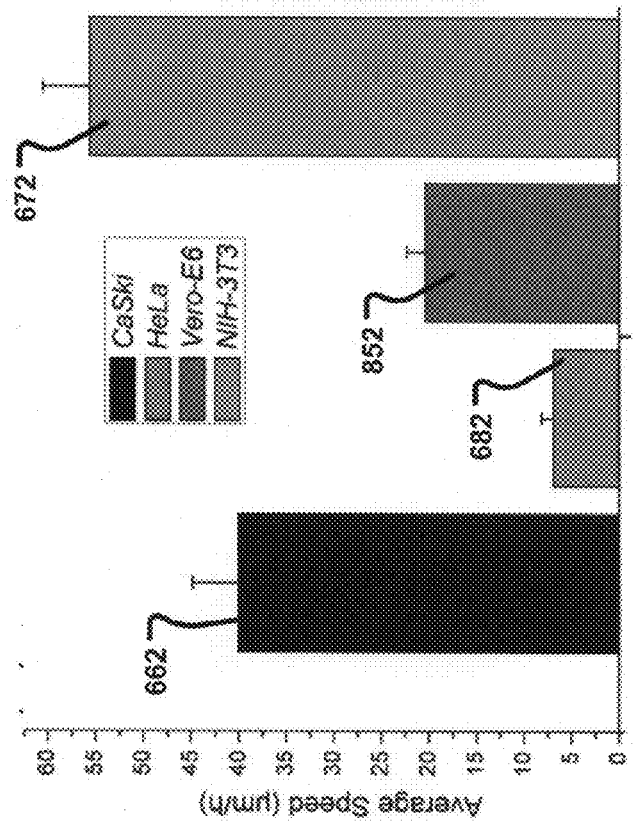

The time for cells starting to migrate (0 hour) until the cells fully cover the whole sensing electrodes (i.e., the time for wound healing of the cell monolayer) is indicated as $t_N$, $t_C$, $t_V$ and $t_H$ for the cell types NIH-3T3, CaSki, Vero-E6 and HeLa respectively. In determining these time periods, the saturation value of the impedance is identified as the value at which the impedance curve remains flat and do not increase more than 2% in the next 5 hours. At this point in time, the measurement of cell migration can be stopped. The average speed (AS) of cell migration can be calculated according to equation (1).

$$AS = R \times t^{-1} \quad (1)$$

where R is the radius of the sensing electrode (100 μm). FIGS. 6C and 6D show the average speed of the four types of cells migration as calculated according to equation (1) for experimental group (1) and group (2), respectively.

FIG. 6C shows, the average speed of cell migration for group (1). FIG. 6B shows the average speed of cell migration for group (2). Because of cell proliferation in the presence of serum (group 1), the measured speed of cell migration is significantly higher than that in serum-free media (group 2). For example, the average speeds for the cell types NIH-3T3 (672), CaSki (662), Vero-E6 (652) and HeLa (682) in the presence of serum are higher than those in absence of serum (674, 664, 654 and 684). Thus, quantitative data on the effect of serum on cell migration speed can be provided.

CaSki and HeLa cells are both human cervical carcinoma cells, and the migration speed of CaSki is higher than that of HeLa cells. Such speed advantage for the CaSki cells over the HeLa cells is present in the serum-containing situation and in the serum-free condition. Fibroblast (such as NIH-3T3) cells have a high migration speed, even higher than some cancer cells in the presence of serum. However, in absence of serum, the CaSki cancer cells have the highest average speed.

Example Application

Real Time Inhibition Assay of Cell Migration

Figure 7A:
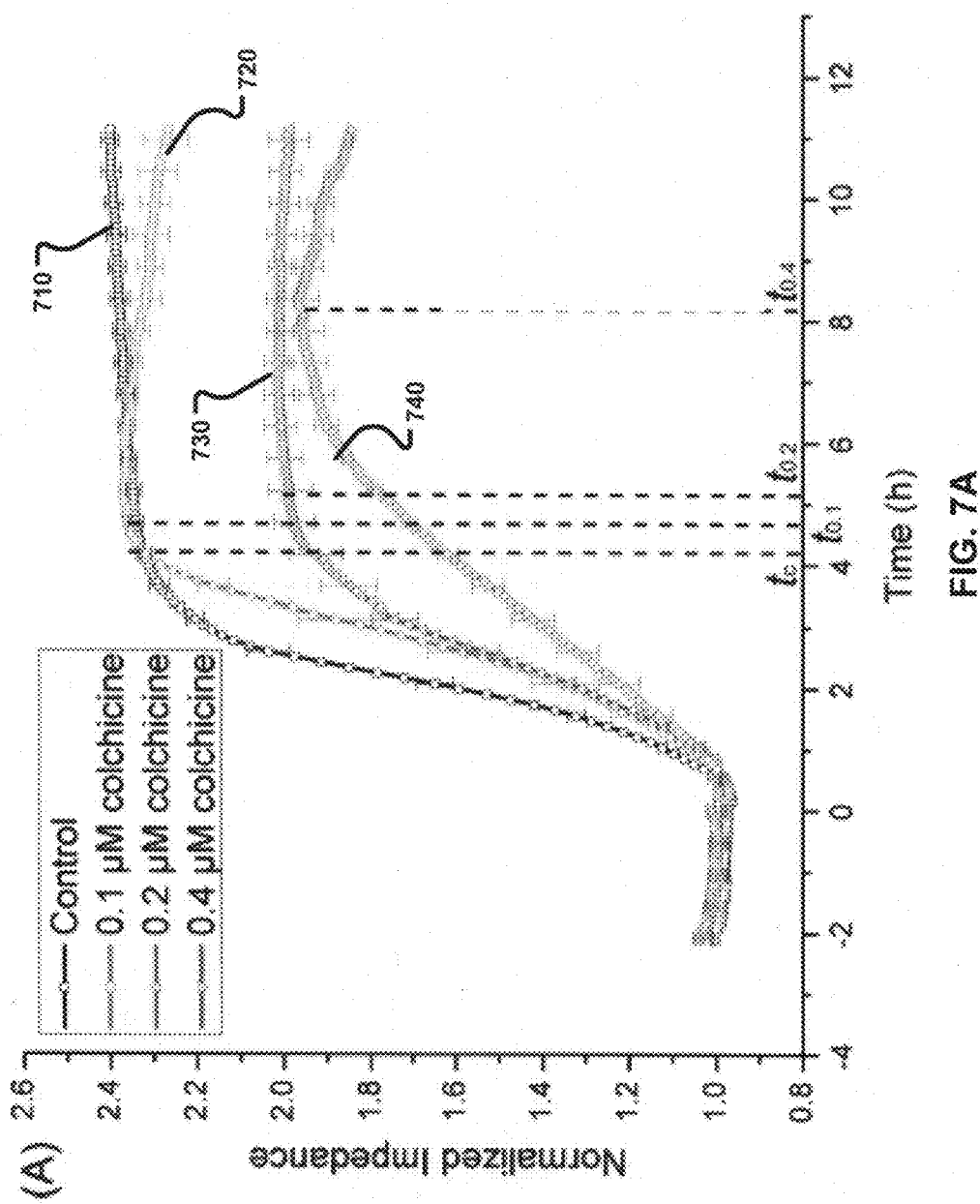
FIGS. 7A and 7B show and example real time inhibition assay of cell migration.

Cell migration can be monitored using a chip based assay. A migration inhibition assay is performed using a migration inhibition agent colchicine to treat Vero-E6 cells. Normalized impedance values are measured in response to different concentrations of colchicines (e.g., control (0 μM), 0.1 μM, 0.2 μM and 0.4 μM) and shown as signals 710, 720, 730 and 740 respectively. Colchicine inhibits cell migration through disruption of microtubules critical for cell migration and cell motion. The inhibitive effect of colchicine upon Vero-E6 cells can be seen in the impedance curves as shown in FIG. 7AA. The time points a which cell migration reaches saturation are shown as $t_c$, $t_{0.1}$, $t_{0.2}$ and $t_{0.4}$ respective.

In FIG. 7(A), the DC current is applied to the electrodes and the SAMs are desorbed at a time of 0 hour. Then after a short time, the impedance starts to increase, which implies that the cells have started to migrate onto the surface of sensor electrodes. Higher the concentration of colchicines, slower the increase in impedance. The time points at which the cells heal a wound for different situations include $t_c$=4.2±0.17 h (control), $t_{0.1}$=4.6±0.19 h (0.1 μM colchicine), $t_{0.2}$=5.1±0.21 h (0.2 μM colchicine) and $t_{0.4}$=8.2±0.42 h (0.4 μM colchicine). These time points represents the times at which the increase in the impedance saturates to indicate near complete migration of cells onto the electrode surface.

Figure 7B:
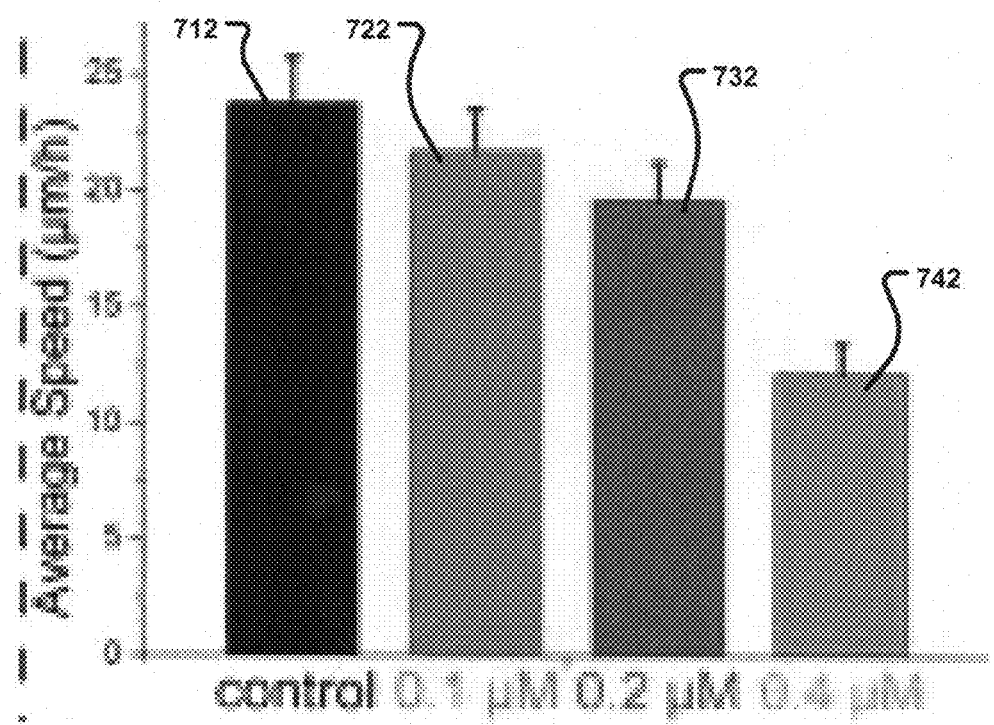
Figure 8A:
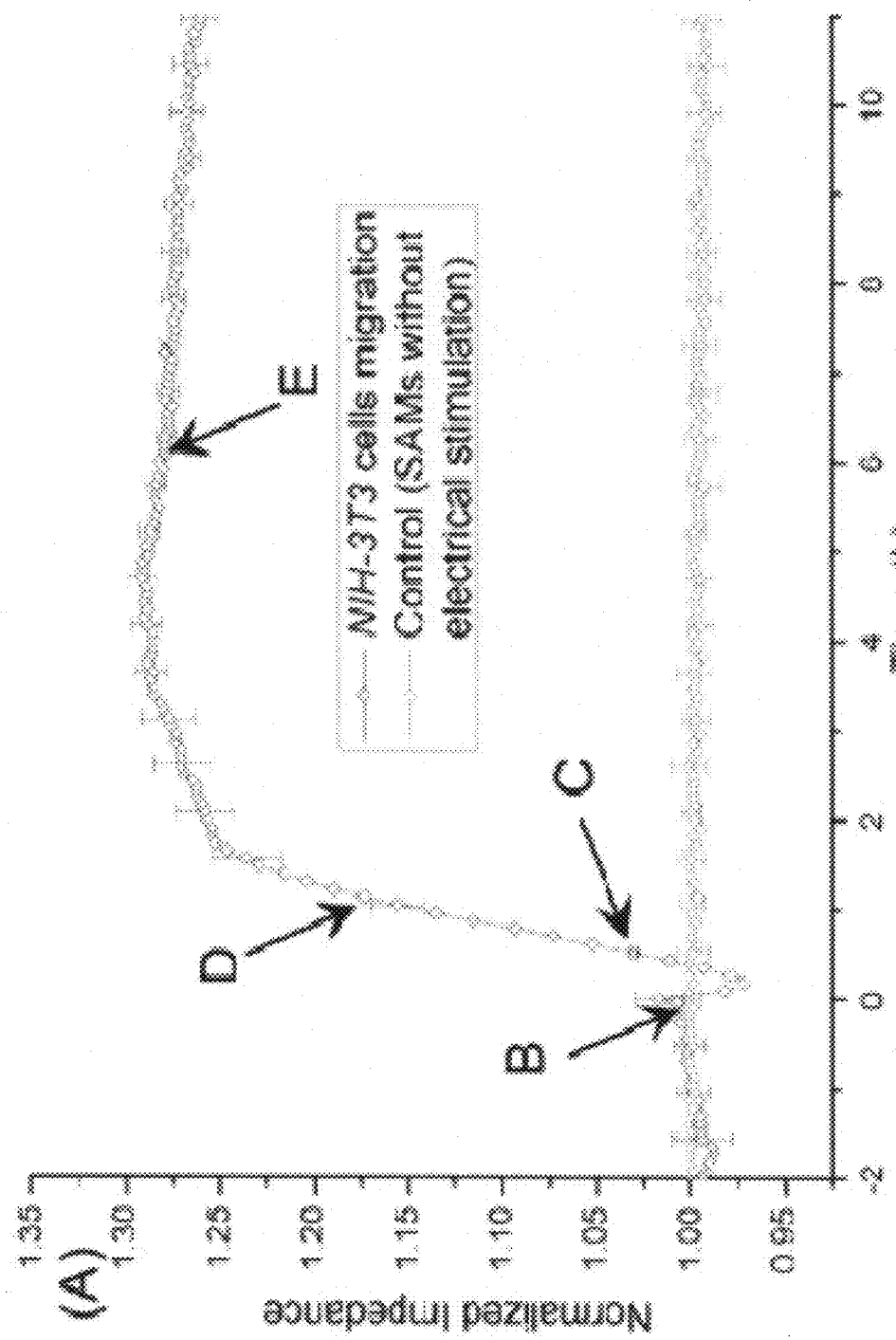

This phenomenon also exhibits the inhibitive effect of colchicine upon the speed of Vero-E6 cell migration as shown in FIG. 7B. The average speed (AS) of cell migration is calculated according to equation (1) and is shown in FIG. 4B. Using this quantitative on-chip cell migration assay, the inhibition effect of cell migration can be quantified using the parameter AS. For example, colchicine inhibits Vero-E6 cell migration in a drug concentration dependant manner.

Example Application

Migration of Fibroblast NIH-3T3 Cells

FIGS. 8A-E show migration of fibroblast NIH-3T3 cells. In this example, a DC current is imposed on the counter electrode to desorb the SAMs from the counter electrode in addition to the sensing electrodes. In response to the desportion of the SAM from the counter electrode, some cells also migrated on the edge of the counter electrode. However, because the total surface area of the counter electrode is made much larger than that of the sensing electrodes, the impedance changes resulting from cell attachment on the counter electrode can be neglected without affecting the accuracy of detection results.

One advantage of this cell migration assay is that retention of cell debris and damaging of cells near the electrode edges can be avoided or minimized.

Testing Cell Viability

Calcein-AM and propidium iodide (PI) were frequently used to test cell viability for the in vitro cell assay. Calcein-AM/PI stock solutions were prepared at concentrations of 1 mM/1 mg mL$^{-1}$ in DMSO/pure water respectively and stored at −20° C. until use. Before usage, cells were washed with PBS buffer and then immersed in a cell culture media containing calcein-AM (10 μM) and PI (2 μM) at 37° C. for 20 min. Images were taken using a fluorescence microscope (DM-IRB, Leica, Germany) and a CCD camera (DP-71, Olympus, Japan).

Materials and Reagents

Pyrex glass wafer can be obtained from Corning Inc. (New York, N.Y.). Polydimethylsiloxane (PDMS, Sylgard 184) can be obtained from Dow Corning Inc (Midland, Mich.). SU-8 photoresist can be obtained from Microchem Inc. (Newton, Mass.). Thiol compound ($HS(CH_2)_{11}(OCH_2CH_2)_6OH$ (abbreviated as EG6) can be obtained from Sigma-Aldrich (St. Louis, Mo.). Calcein-AM and propidium iodide (PI) can be obtained from Invitrogen (Carlsbad, Calif.). Dulbecco's modified Eagle's medium, RPMI-1640 media, bovine calf serum, fetal bovine serum and trypsin/EDTA solution can be obtained from Gibco BRL Inc. (Grand Island, N.Y.).

Only a few implementations have been described. The techniques, systems and apparatus for detecting migration are applicable in additional implementations. A device for monitoring cell migration can include at least one conductive electrode provide on a surface of the substrate. The at least one electrode is surrounded by insulating material. The device can be treated to apply a chemical coating to the electrodes after which a layer of cells is allowed to grow on the surface of the device. Once the cells have grown over the surfaces, an electrical signal is applied to the electrodes, which causes the chemical coating to desorb from the electrodes. This provides a cell-free electrode surface surrounded by healthy cells growing on the adjacent insulation. The electrodes can then be monitored as the cells grow or migrate across the electrodes. Cells growing on the electrodes cause measurable changes in, e.g., impedance; consequently, cell migration or spreading can be monitored by monitoring electrical properties of the electrodes.

Cell contact or adherence on the surface of the electrode is inhibited or reduced by the coating applied on the electrode surface. The stimulation of the electrodes can be applied for a length of time and voltage adequate to desorb greater than 70%, 80%, 90%, 95%, 98% or about 100% of the coating or cells from the surface of the electrode. The coating on the surface of the electrode inhibits positioning of cells onto the surface of the electrode or the surface of the coating. For example, contacting of the cells onto the surface of the electrode or coating is limited to 0%, 2%, 5%, 10%, 25%, 40% or about 50% of the surface area of the electrode or coating. The electrode can be stimulated with an electrical signal such that any chemical coating and/or cell is desorbed from the surface electrode. In other embodiments, the electrical property is impedance, resistance, capacitance, inductance or frequency; and an instrument capable of measuring the property is in communication with the electrodes. In another embodiment, the electrical property is impedance.

The substrate of the device can include a non-conductive layer or layers on the surface of the substrate. The electrode can include one or more sensing electrodes and one or more counter electrodes. The counter electrode surface area can be at least 2 times the surface area of the sensing electrodes. In some embodiments, the device includes at least 10 sensing electrodes an at least one counter electrode.

The coating can be applied to the sensing electrode alone, counter electrode alone or both. Also, the speed of cell migration can be calculated from the average electrical signals of at least two sensing electrodes. Cell migration can be monitored by measuring the rate at which a cell migrates across a surface. Further, an artificial wound can be created to measure cell migration as a result of the formation of the artificial wound.

Artificial wound refers to the simulation of an area wherein cells border another area without cells. The wound edge refers to the border between the two areas. The wound edge may also refer to the nearby region of the border. The artificial wound might be created through physical removal of a portion of cells from a cellular colony. It also may be created through prevention of cellular growth, adherence to, or spreading to a particular area.

The cell migration detection device and techniques described in this specification can be used to probe biological phenomena including embryogenesis, wound healing, inflammatory response and tumor metastasis. Cell migration detection is applicable for other technological applications, such as tissue engineering.

On-chip cell migration assay using self-assembled monolayer chemical modification can be combined with real-time cellular impedance sensing. For example, cell migration can be monitored using quantitative migration data and may be used in a high-throughput and fully-automatic application. In addition, techniques of SAMs and real-time cellular impedance sensing in cell migration assays can be used. Further, the on-chip cell migration assay can be used to evaluate the inhibition effect of potential drugs in real-time which is of benefit for anti-migratory drug screening and drug discovery.

The cell migration device can be used in a high-throughput screening application. In one embodiment, high-throughput screening comprises screening a plurality of test compounds for an effect on cellular response. High-throughput screening may be carried out in microfluidic devices or microlaboratory systems, which allow for integration of the elements required for performing the assay, automation, and minimal environmental effects on the assay system, e.g., evaporation, contamination, human error. Specific configuration of these devices may vary depending upon the type of assay and/or assay orientation desired. For example, in some embodiments, the screening methods of the invention can be carried out using a microfluidic device having two intersecting channels. For more complex assays or assay orientations, multichannel/intersection devices may be employed. The small scale, integratability and self-contained nature of these devices allows for virtually any assay orientation to be realized within the context of the microlaboratory system as described in U.S. Pat. No. 7,285,411, the contents of which are.

In some implementations, deposition of the coating onto the surface of the electrode is performed using the techniques described in U.S. Pat. No. 5,523,878, the contents of which are incorporated by reference. Briefly, the surface of the electrode is cleaned to remove contaminants. This may entail conventional cleaning techniques, using dry processing or solution-based processing. A solution is prepared, which contains the molecular precursor species for the formation of the coating on the surface of the electrode. This solution can be used for liquid deposition of the precursor, which results in the coating of the surface of the electrodes. The precursor solution may also contain a solvent for decreasing the surface energy of the solution, with the added benefit that the solvent may be selected so as to remove unwanted residue. In addition, the precursor solution may contain a surfactant for decreasing surface tension of the solution. The precursor solution can be selected to avoid crystallization or aggregation of the precursor molecules, such as perfluorinated solvents. Examples of a perfluorinated solvent include perfluorohexane, PF5060 (Minnesota Mining and Manufacturing Company (3M)), Vertrel XF (Du Pont), and perfluorinated alkanes.

Coating of the electrode surfaces can include liquid deposition, in which the surfaces to be coated are immersed in or contacted with the precursor solution. In some embodiments, the deposition is performed by immersing the entire device in the solution. However, any method that contacts the precursor solution with at least the surfaces to be coated is suitable. The device remains in contact with the precursor solution for a time sufficient to allow the electrode surfaces to be coated or for formation of a self-assembled monolayer. The required time can be determined experimentally, and depends on the materials involved. In general, the device is left in the precursor solution for at least a period of time sufficient to permit saturation of the surfaces to be coated. The coating of the electrode surfaces may be formed by techniques other than immersion. For example, nebulizing the precursor solution and subjecting the surfaces to be coated to the resulting droplets may permit the same self-assembly of the chemical onto the surface of the electrode as immersion.

The liquid deposition can result in the spontaneous formation of a monolayer. Because of the coordination chemistry between the precursor and the surfaces to be coated, chemical bond formation occurs and anchors the precursor molecules to these surfaces. In some embodiments, the molecules of the precursor solution attempt to occupy every available binding site on the surfaces to which the solution is exposed. Also, removal of the device from contact with the precursor solution may be followed by a rinsing with a solvent to remove excess precursor solution from the surface of the device.

In addition to the chemical compounds described above many other compounds can be used. The coating can include one or more of the above specified formulas. The coating compound can be selected to give the coating the ability to form a layer on the surface of the electrode material and to a possess the desired coating properties described above.

For example, the coating can include a compound containing at least one head group and at least one tail group. The head group can include a group that has affinity for the electrode surface. Examples of a head group include —S— or —SH, with both have an affinity to gold. Also, the tail group can be hydrophilic, such as —(OCH$_2$CH$_2$)$_6$—, hydrophobic, such as —(CH$_2$)$_{11}$—, or a mixture of hydrophilic and hydrophobic portions, such as —(CH$_2$)$_{11}$—(OCH$_2$CH$_2$)$_6$—.

In some embodiments, the coating can include a compound containing at least one head group and at least one tail group. Also, the coating can include a thiol containing compound, generally a lipophilic hydrocarbyl group tail group substituted with at least one —SH head group. The compound also includes at least one hydrophilic functional group, such as —OH, COOH, or NH$_2$.

In some embodiments, the coating comprises a compound selected from the group consisting of R(X)SH,
R(X)S(X)S(X)R,
R(OX)$_m$SH,
R(X)(OX)$_m$SH, and
R(XO)$_m$(X)SH; wherein each X is selected from the group consisting of C1-C20 alkylene, C2-C20 alkenylene, and C2-C20 alkynylene; wherein each alkylene, alkenylene and alkynylene may be optionally substituted, fluorinated, branched, cyclic or a combination of these; wherein each R is independently selected from a group consisting of H, C1-C20 alkyl, OC1-C20 alkyl, OH, COOH, NH$_2$, CF$_3$ and halo.

The coating can include R(C2-C6 alkyleneO)$_m$(C1-C20 alkylene)SH, such as HO(CH$_2$CH$_2$O)$_6$(CH$_2$)$_{11}$SH, or R(C1-C20 alkylene)(OC2-C6 alkylene)$_m$SH. In some embodiments, m is 0-10. In other embodiments, m is 3-10. In yet other embodiments, m is 4-8. The number of carbons in the alkylene, alkenylene or alkynylene may be any desired integer depending on the desired character of the layer to be formed.

Example compounds can include saturated hydrocarbyl groups having at least 10 carbon atoms and at least one SH group. Also example compounds can include at least 12 carbon atoms, at least one O in an ether linkage, and at least one SH group.

Monitoring cell migration can include contacting cells on the surface of the device described above; stimulating the electrode with an electrical signal such that any chemical coating and/or cell is desorbed from the electrode surface; and monitoring at least one electrical property of the electrodes over a period of time to allow the cells to migrate and/or grow. The cells can be positioned on the surface of the substrate adjacent to the electrode with few or no cells on the surface of the electrode.

In alternative embodiments, a method of monitoring cell migration described herein may be used in an automated or high-throughput application, wherein at least two said electrodes are distributed over the surface of said substrate. In alternative embodiments, a method of cell migration described herein may be used in an automated or high-throughput application, wherein multiple sensing devices can be used simultaneously. In alternative embodiments, monitoring of the electrical property is carried out in real time and may be used to calculate the speed of migration of cells on the surface of the electrodes. In some embodiments, the rate of cell migration is calculated from the average rate of cell migration from sensing electrodes on the device.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this application.

The invention claimed is:

1. A microelectrode sensing device, comprising:
    a substrate;
    an array of microelectrode sensors formed on the substrate, each sensor comprising at least one conductive layer formed above the substrate and patterned to comprise a counter electrode and a plurality of sensing electrodes to detect an electrical signal in absence and presence of one or more target cells positioned on at least a portion of a surface of each sensing electrode; and
    a chemical coating on a first region of the surface of each of the plurality of sensing electrodes to inhibit adhesion of the one or more target cells onto the first region of the surface of the plurality of sensing electrodes, while a second region of the surface of each of the plurality of sensing electrodes is free of the chemical coating to allow adhesion of the one or more target cells onto the second region of the surface of the plurality of sensing electrodes, and wherein the chemical coating is made of a material that desorbs from the surface of the plurality of sensing electrodes in response to an electrical stimulus;
    wherein the plurality of sensing electrodes are spaced apart and arranged around the counter electrode and each sensing electrode having one end facing the counter electrode and a second end facing away from the counter electrode, the second end commonly connected to second ends of all other sensing electrodes to collectively provide a single spatially averaged output value of the detected electrical signal, and
    wherein the first region of the surface of each sensing electrode is located at the end of each sensing electrode facing the counter electrode, and
    wherein the second region of the surface of each sensing electrode is adjacent to the first region and extended to the second end of each sensing electrode.

2. The microelectrode sensing device of claim 1, wherein the plurality of sensing electrodes comprise a plurality of concentric sensing electrodes.

3. The microelectrode sensing device of claim 1, comprising one or more layers of insulating material formed between the plurality of sensing electrodes to electrically insulate the plurality of sensing electrodes from each another.

4. The microelectrode sensing device of claim 1, wherein the at least one conductive layer is patterned to comprise the counter electrode and the plurality of sensing electrodes in a ratio of 1 counter electrode to N sensing electrodes, where N is a positive integer.

5. The microelectrode sensing device of claim 1, wherein the at least one conductive layer is patterned to comprise the counter electrode and the plurality of sensing electrodes so as to provide a total surface area of the counter electrode that is at least twice a total surface area of the plurality of sensing electrodes.

6. The microelectrode sensing device of claim 1, wherein the at least one conductive layer is patterned to comprise the counter electrode and the plurality of sensing electrodes to detect a change in the electrical signal in response to the one or more target cells migrating onto the surface of the plurality of sensing electrodes from an area outside of the surface of the sensing electrodes.

7. The microelectrode sensing device of claim 1, wherein the at least one conductive layer is patterned to comprise the counter electrode and the plurality of sensing electrodes to detect an impedance to a flow of the electrical signal in response to the one or more target cells migrating onto the surface of the sensing electrodes from an area outside of the surface of the sensing electrodes.

8. The microelectrode sensing device of claim 1, wherein the chemical coating comprises a self-assembled monolayer or bi-layer.

9. The microelectrode sensing device of claim 1, wherein the plurality of sensing electrodes comprise sensing electrodes arranged to form a concentric shape around the counter electrode located at a center of the concentric shape.

10. The microelectrode sensing device of claim 9, wherein the plurality of sensing electrodes are at an equal distance away from each other.

11. The microelectrode sensing device of claim 1, wherein each sensing electrode is at an equal radial distance away from a center of the counter electrode.

12. The microelectrode sensing device of claim 1, wherein the plurality of sensing electrodes are symmetrical in shape and similarly sized to provide uniform impedance measurement from one electrode to another.

13. A system comprising:
a microelectrode sensing device comprising:
a substrate, and
an array of microelectrode sensors formed on the substrate, each sensor comprising at least one conductive layer formed above the substrate and patterned to comprise a counter electrode and a plurality of sensing electrodes to detect an electrical signal in absence and presence of one or more target cells positioned on at least a portion of a surface of each sensing electrode,
wherein the plurality of sensing electrodes are spaced apart, arranged around the counter electrode such that one end of each electrode is collectively connected to end of a common output to provide a single spatially averaged output value of the detected electrical signal; and
an analysis system in communication with the microelectrode sensing device to
receive from the microelectrode sensing device data representing at least the electrical signal detected by the sensing electrodes, and
process the received data to obtain one or more impedance measurements;

wherein the microelectrode sensing device comprises a chemical coating on a first region of the surface of each of the plurality of sensing electrodes to inhibit adhesion of the one or more target cells onto the first region of the surface of the plurality of sensing electrodes, while a second region of the surface of each of the plurality of sensing electrodes is free of the chemical coating to allow adhesion of the one or more target cells onto the second region of the surface of the plurality of sensing electrodes, and wherein the chemical coating is made of a material that desorbs from the surface of the plurality of sensing electrodes in response to an electrical stimulus, and
wherein the first region of the surface of each sensing electrode is located at a second end of each sensing electrode facing the counter electrode, and
wherein the second region of the surface of each sensing electrode is adjacent to the first region and extended to the second end of each sensing electrode.

14. The system of claim 13, wherein the analysis system is configured to receive the data representing at least the electrical signal detected by the sensing electrodes in absence of the target cells to establish a control impedance measurement.

15. The system of claim 14, wherein the analysis system is configured to receive in real-time, the data representing at least the electrical signal detected by the sensing electrodes over a period of time corresponding to migration of the one or more target cells onto the surface of the sensing electrodes from a location external to the surface.

16. The system of claim 15, wherein the analysis system is configured to process the data received in absence of target cells and the data received over the period of time corresponding to migration of the one or more target cells to identify a change in impedance corresponding to the migration of the one or more target cells.

17. The system of claim 13, wherein the chemical coating comprises a self-assembled monolayer or bi-layer.

18. The system of claim 13, wherein the analysis system is configured to apply the electrical stimulus to the sensing electrodes to desorb the chemical coating.

19. A method for monitoring cell migration comprising:
applying a chemical coating layer on a first region of a surface of each sensing electrode in a microelectrode sensing device that includes a counter electrode and a plurality of sensing electrodes to inhibit adhesion of target cells on the first region of the surface of each sensing electrode, while a second region of the surface of each of the plurality of sensing electrodes is free of the chemical coating to allow adhesion of the one or more target cells onto the second region of the surface of the plurality of sensing electrodes;
seeding the target cells in the microelectrode sensing device to allow the seeded target cells to adhere to areas outside of the surface of each sensing electrode;
applying an electrical signal to each sensing electrode to desorb the applied chemical coating layer from the surface of each sensing electrode;
detecting a change in an electrical impedance measured by each sensing electrode in response to one or more of the seeded target cells migrating onto the surface of each sensing electrode; and
receiving a single spatially averaged output value of a detected electrical signal from the plurality of sensing electrode, wherein the plurality of sensing electrodes are spaced apart and arranged around the counter electrode and connected to one another to provide the single spatially averaged output value, wherein the first region of the surface of each sensing electrode is located at one end of each sensing electrode facing the counter electrode, and wherein the second region of the surface of each sensing electrode is adjacent to the first region and extended to the second end of each sensing electrode.

20. The method of claim 19, wherein applying the chemical coating comprises applying a layer of thiol based compound.

21. The method of claim 19, further comprising applying the chemical coating on a surface of the counter electrode in the microelectrode sensing device.

22. The method of claim 19, wherein applying the chemical coating comprise applying one or more self-assembled monolayers.

23. The method of claim 19, comprising measuring a background impedance value before seeding the target cells.

24. The method of claim 23, comprising calculating a normalized impedance value based on the background impedance value.

25. The method of claim 19, comprising detecting the change in the electrical impedance in real time as the one or more of the seeded target cells migrate onto the surface of each sensing electrode until a steady state impedance is reached.

26. The method of claim 19, wherein detecting the change in the electrical impedance measured by each sensing electrode comprises applying another electrical signal to each sensing electrode.

27. The Method of claim 26, wherein applying the other electrical signal comprises in response to the other electrical signal applied to each sensing electrode, receiving a sensed signal from each sensing electrode and averaging the sensed signals to obtain an average impedance measurement due to the one or more of the seeded target cells migrate onto the surface of each sensing electrode.

28. The method of claim 27, comprising determining a speed of cell migration based on the obtained average impedance measurement.

29. The method of claim 19, comprising arranging the plurality of sensing electrodes in a concentric shape around the counter electrode.

* * * * *